(12) United States Patent
Hitchcock et al.

(10) Patent No.: US 8,258,306 B2
(45) Date of Patent: Sep. 4, 2012

(54) GLYCINE TRANSPORTER-1 INHIBITORS

(75) Inventors: Stephen A. Hitchcock, Jupiter, FL (US); Wenyuan Qian, Camarillo, CA (US); Albert Amegadzie, Moorpark, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 12/746,755

(22) PCT Filed: Dec. 11, 2008

(86) PCT No.: PCT/US2008/013596
§ 371 (c)(1),
(2), (4) Date: Aug. 12, 2010

(87) PCT Pub. No.: WO2009/075857
PCT Pub. Date: Jun. 18, 2009

(65) Prior Publication Data
US 2010/0298341 A1    Nov. 25, 2010

Related U.S. Application Data

(60) Provisional application No. 61/007,306, filed on Dec. 12, 2007, provisional application No. 61/191,179, filed on Sep. 5, 2008.

(51) Int. Cl.
*C07D 211/34* (2006.01)
(52) U.S. Cl. ........................................ 546/239
(58) Field of Classification Search .................. None
See application file for complete search history.

(56) References Cited

U.S. PATENT DOCUMENTS

| | | |
|---|---|---|
| 4,988,689 A | 1/1991 | Janssens et al. |
| 5,272,150 A | 12/1993 | Janssens et al. |
| 5,633,266 A | 5/1997 | Baker et al. |
| 6,001,854 A | 12/1999 | Ognyanov et al. |
| 6,350,761 B1 | 2/2002 | Guilford et al. |
| 6,797,713 B2 | 9/2004 | Scannell et al. |
| 7,087,596 B2 | 8/2006 | Michel et al. |
| 7,132,551 B2 | 11/2006 | Aquila et al. |
| 7,355,042 B2 | 4/2008 | Edgar et al. |
| 7,538,114 B2 | 5/2009 | Hitchcock et al. |
| 2002/0045610 A1 | 4/2002 | Hansen et al. |
| 2007/0203100 A1 | 8/2007 | Pan et al. |
| 2007/0208003 A1 | 9/2007 | Bell et al. |

FOREIGN PATENT DOCUMENTS

| | | |
|---|---|---|
| JP | 05148234 A | 6/1993 |
| WO | WO 9745423 A1 | 12/1997 |
| WO | WO 0222572 A2 | 3/2002 |
| WO | WO 03032912 A2 | 4/2003 |
| WO | WO 03053942 A1 | 7/2003 |
| WO | WO 200702206841 | 2/2007 |
| WO | WO 2008009435 A1 | 1/2008 |

OTHER PUBLICATIONS

Silverman, R. B., The Organic Chemistry of Drug Design and Drug Action: Chapter 2, Drug Discovery, Design and Development, Academic Press, pp. 5-51 (1992).*

* cited by examiner

*Primary Examiner* — Janet Andres
*Assistant Examiner* — Timothy R Rozof
(74) *Attorney, Agent, or Firm* — Elsa D. Lemoine

(57) ABSTRACT

The present invention provides compounds that are glycine transporter 1 (hereinafter referred to as GlyT-1) inhibitors and are therefore useful for the treatment of diseases treatable by inhibition of GlyT1 such as cognitive disorders associated with Schizophrenia, ADHD (attention deficit hyperactivity disorder), MCI (mild cognitive impairment), and the like. Also provided are pharmaceutical compositions containing such compounds and processes for preparing such compounds.

11 Claims, No Drawings

GLYCINE TRANSPORTER-1 INHIBITORS

CROSS-REFERENCE TO RELATED APPLICATIONS

This application is a 35 U.S.C. §371 application of PCT/US2008/013596, filed on Dec. 11, 2008, which claims the benefit under 35 U.S.C. 119(e) of U.S. provisional application Nos. 61/007,306 filed Dec. 12, 2007 and 61/191,179 filed Sep. 5, 2008. The entire contents of these related applications are hereby incorporated by reference herein.

FIELD OF THE INVENTION

The present invention provides compounds that are Glycine Transporter 1 (hereinafter referred to as GlyT-1) inhibitors and are therefore useful for the treatment of diseases treatable by inhibition of GlyT1 such as cognitive disorders associated with Schizophrenia, ADHD (attention deficit hyperactivity disorder), and MCI (mild cognitive impairment). Also provided are pharmaceutical compositions containing such compounds and processes for preparing such compounds.

BACKGROUND

Glycine is a principal inhibitory neurotransmitter in the mammalian CNS, but also serves as endogenous obligatory co-agonist with glutamate for activating N-methyl-D-aspartate (NMDA) receptors. The synaptic actions of glycine end through the activity of high affinity transporters located in neuronal and glial membranes. The glycine transporter type 1 (GlyT1) is involved in glycine re-uptake processes at the level of excitatory synapses. Blockade of GlyT1 increases glycine concentration at excitatory synapses, thus potentiating NMDA neurotransmission. Since schizophrenia has been associated with hypofunction of NMDA receptors in such brain regions as prefrontal cortex and hippocampus, an inhibitor of GlyT1 would restore normal NMDA transmission and thereby reduce schizophrenia symptoms. In addition to schizophrenia, GlyT1 inhibitors can be used in other conditions characterized by impaired NMDA transmission, such as broad cognitive deficits (including MCI) and Alzheimer's disease.

Existing therapeutics for schizophrenia are efficacious only at treating positive symptoms of the disease. Negative symptoms, including flattened affect, social withdrawal as well as cognitive deficits are not ameliorated by current medications, which primarily target the mesolimbic dopamine system. Therefore, novel treatments for schizophrenia are needed to specifically improve negative symptoms and cognitive deficits associated with the disease. The present invention fulfills this need and related needs.

SUMMARY

In one aspect, provided are compounds of Formula (I):

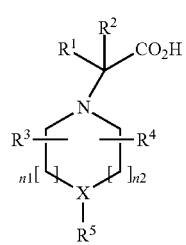

(I)

wherein:
X is —CH— or —N—;
$R^1$ and $R^2$ are independently hydrogen or alkyl;
$R^3$ and $R^4$ are independently hydrogen, alkyl, haloalkyl, alkoxy, or haloalkoxy;
n1 is 0 or 1 and n2 is 1 or 2 provided that when X is —N— then n1 and n2 are 1; and (i) when X is —CH—, then $R^5$ is —CHAr$^1$Ar$^2$ or —NAr$^1$Ar$^2$ where Ar$^1$ and Ar$^2$ are independently aryl, heteroaryl, cycloalkyl, or heterocyclyl where each of the aforementioned ring is optionally substituted with $R^a$, $R^b$ or $R^c$ where $R^a$ is alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and $R^b$ and $R^c$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl and where the aromatic or alicyclic ring in $R^a$, $R^b$ and $R^c$ is optionally substituted with $R^d$, $R^e$ or $R^f$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino; and (ii) when X is —N— or —CH—, then $R^5$ is:
(a) a ring of formula (i), (ii), or (iii):

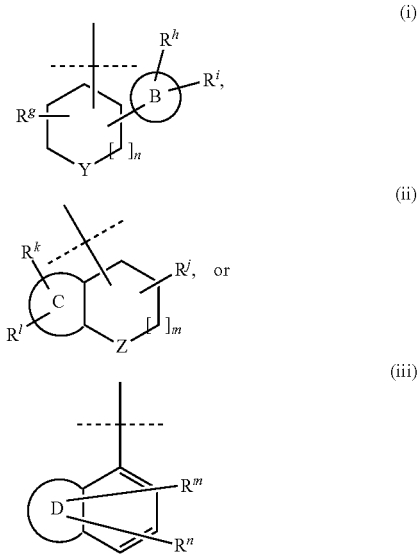

where:
n and m are independently 0-2;
ring B, C, or D is phenyl or a 5- or 6-membered heteroaryl ring;
Y and Z are independently —CH$_2$—, —O—, —NH—, —S— —SO—, or —SO$_2$—; and
two of $R^g$, $R^h$, and $R^i$; $R^j$, $R^k$, and $R^l$; and one of $R^m$ and $R^n$ are independently hydrogen, alkyl, halo, haloalkyl, haloalkoxy, alkylthio, cyano, alkoxy, amino, monosubstituted amino, disubstituted amino, acyl, carboxy, or alkoxycarbonyl and the remaining of $R^g$, $R^h$, and $R^i$; $R^j$, $R^k$, and $R^l$; and $R^m$ and $R^n$ is hydrogen, alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl and where the aromatic or alicyclic ring in $R^g$, $R^h$, $R^i$, $R^j$, $R^k$, $R^l$, $R^m$ and $R^n$ is optionally substituted with $R^o$, $R^p$ and $R^q$ which are independently alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino; or (b) a ring of formula (iv), (v), (vi), (vii), (viii), or (ix):

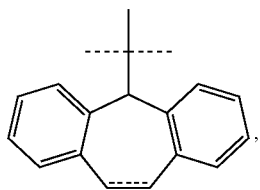
(iv)

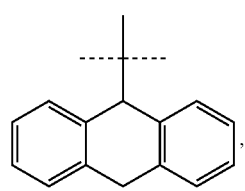
(v)

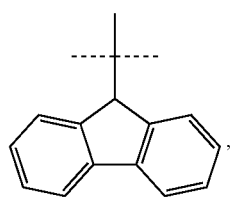
(vi)

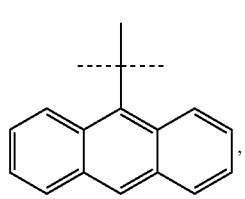
(vii)

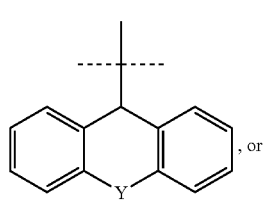
(viii)

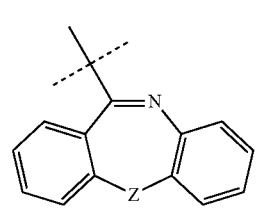
(ix)

where:

in rings (iv), (v), (vi), (vii), (viii), or (ix), one or two carbon ring atom(s) can optionally be replaced by nitrogen atom(s) or one or two of the phenyl ring(s) in the rings can optionally be replaced independently by thienyl or thiazolyl ring(s);

- dashed line in the ring of formula (iv) is an optional bond;

Y and Z are independently —$CH_2$—, —O—, —NH—, —S— —SO—, or —$SO_2$—; and ring (iv), (v), (vi), (vii), (viii), and (ix) are independently substituted with $R^r$, $R^s$ and $R^t$ where $R^r$ and $R^s$ are independently hydrogen, alkyl, halo, haloalkyl, haloalkoxy, alkylthio, cyano, alkoxy, amino, monosubstituted amino, disubstituted amino, acyl, carboxy, or alkoxycarbonyl and $R^t$ is hydrogen, alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl and where the aromatic or alicyclic ring in $R^r$, $R^s$, and $R^t$ is optionally substituted with $R^u$, $R^v$, or $R^w$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino; or a pharmaceutically acceptable salt thereof provided that: the compound of Formula (I) is not 2-(4-benzhydrylpiperidin-1-yl)acetic acid; 2-(4-(naphthalen-1-yl)piperazin-1-yl) acetic acid; 2-(3-benzhydrylpiperidin-1-yl)acetic acid, and

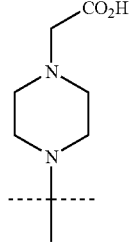

where $R^5$ is a ring of formula:

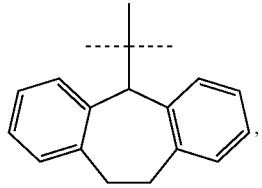

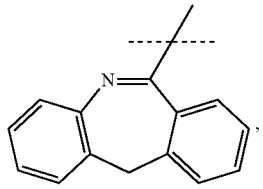

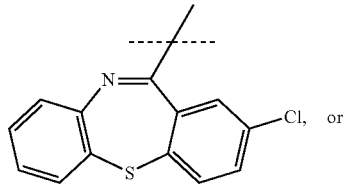
Cl, or

-continued

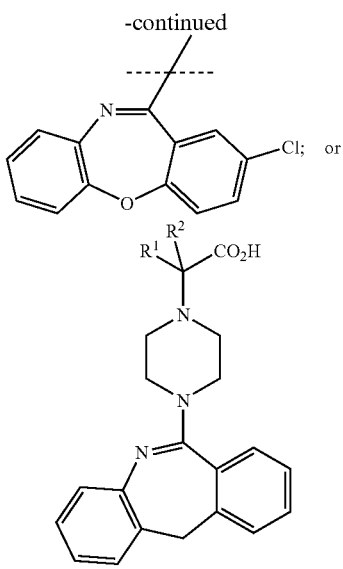

where R¹ is hydrogen and R² is methyl or R¹ and R² are methyl.

In a second aspect, this invention is directed to a pharmaceutical composition comprising a compound of Formula (I), a pharmaceutically acceptable salt thereof or a mixture a compound of Formula (I) and a pharmaceutically acceptable salt thereof; and a pharmaceutically acceptable excipient.

In a third aspect, this invention is directed to a method of treating a disease treatable by inhibition of GlyT1 receptor in a patient which method comprises administering to the patient a pharmaceutical composition comprising a compound of Formula (I):

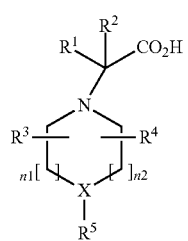

(I)

wherein:

X is —CH— or —N—;

$R^1$ and $R^2$ are independently hydrogen or alkyl;

$R^3$ and $R^4$ are independently hydrogen, alkyl, haloalkyl, alkoxy, or haloalkoxy;

n1 is 0 or 1 and n2 is 1 or 2 provided that when X is —N— then n1 and n2 are 1; and (i) when X is —CH—, then $R^5$ is —CHAr¹Ar² or —NAr¹Ar² where Ar¹ and Ar² are independently aryl, heteroaryl, cycloalkyl, or heterocyclyl where each of the aforementioned ring is optionally substituted with $R^a$, $R^b$ or $R^c$ where $R^a$ is alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and $R^b$ and $R^c$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl and where the aromatic or alicyclic ring in $R^a$, $R^b$ and $R^c$ is optionally substituted with $R^d$, $R^e$ or $R^f$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino; and (ii) when X is —N— or —CH—, then $R^5$ is:

(a) a ring of formula (i), (ii), or (iii):

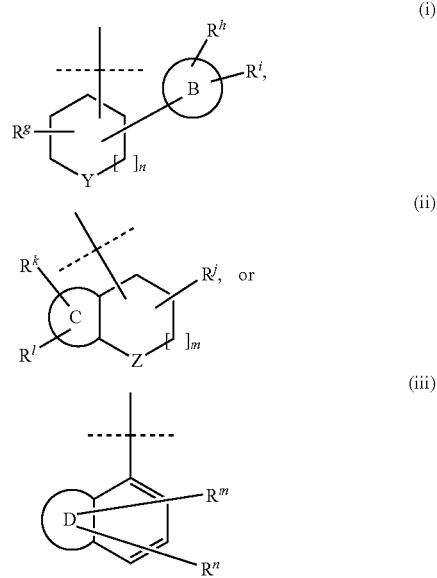

where:

n and m are independently 0-2;

ring B, C, or D is phenyl or a 5- or 6-membered heteroaryl ring;

Y and Z are independently —CH₂—, —O—, —NH—, —S— —SO—, or —SO₂—; and two of $R^g$, $R^h$, and $R^i$; $R^k$, and $R^l$; and one of $R^m$ and $R^n$ are independently hydrogen, alkyl, halo, haloalkyl, haloalkoxy, alkylthio, cyano, alkoxy, amino, monosubstituted amino, disubstituted amino, acyl, carboxy, or alkoxycarbonyl and the remaining of $R^g$, $R^h$, and $R^i$; $R^j$, $R^k$, and $R^l$; and $R^m$ and $R^n$ is hydrogen, alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl and where the aromatic or alicyclic ring in $R^g$, $R^h$, $R^i$, $R^k$, $R^l$, $R^m$ and $R^n$ is optionally substituted with $R^o$, $R^p$ and $R^q$ which are independently alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino; or (b) a ring of formula (iv), (v), (vi), (vii), (viii), or (ix):

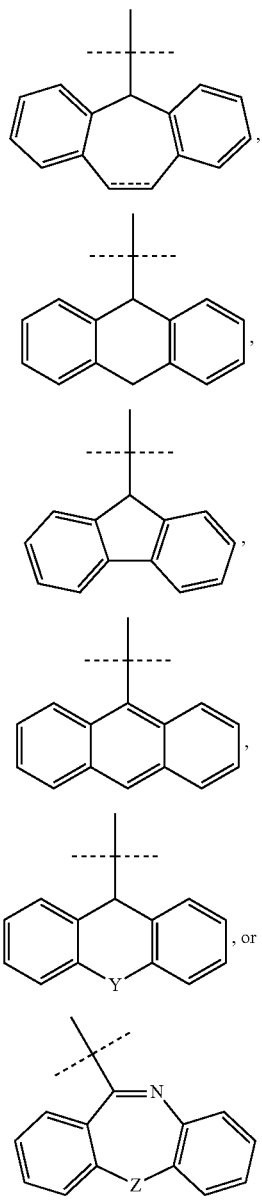

where:
in rings (iv), (v), (vi), (vii), (viii), or (ix), one or two carbon ring atom(s) can optionally be replaced by nitrogen atom(s) or one or two of the phenyl ring(s) in the rings can optionally be replaced independently by thienyl or thiazolyl ring(s);
- dashed line in the ring of formula (iv) is an optional bond;
Y and Z are independently —CH$_2$—, —O—, —NH—, —S— —SO—, or —SO$_2$—; and
ring (iv), (v), (vi), (vii), (viii), and (ix) are independently substituted with R$^r$, R$^s$ and R$^t$ where R$^r$ and R$^s$ are independently hydrogen, alkyl, halo, haloalkyl, haloalkoxy, alkylthio, cyano, alkoxy, amino, monosubstituted amino, disubstituted amino, acyl, carboxy, or alkoxycarbonyl and R$^t$ is hydrogen, alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl and where the aromatic or alicyclic ring in R$^r$, R$^s$ and R$^t$ is optionally substituted with R$^u$, R$^v$ or R$^w$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino; or
a pharmaceutically acceptable salt thereof.

In one embodiment the disease is ADHD (attention deficit hyperactivity disorder), MCI (mild cognitive impairment), or cognitive disorders associated with Schizophrenia.

In a fourth aspect, this invention provides above compounds for use as a medicament.

In a fifth aspect, this invention provides above compounds for preparing a medicament for treating ADHD (attention deficit hyperactivity disorder), MCI (mild cognitive impairment), or cognitive disorders associated with Schizophrenia.

DETAILED DESCRIPTION

Definitions

Unless otherwise stated, the following terms used in the specification and claims are defined for the purposes of this application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

"Alicyclic" means a non-aromatic ring e.g., cycloalkyl or heterocyclyl ring.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkylthio" means a —SR radical where R is alkyl as defined above, e.g., methylthio, ethylthio, and the like.

"Alkylsulfonyl" means a —SO$_2$R radical where R is alkyl as defined above, e.g., methylsulfonyl, ethylsulfonyl, and the like.

"Amino" means a —NH$_2$.

"Alkylamino" means a —NHR radical where R is alkyl as defined above, e.g., methylamino, ethylamino, propylamino, or 2-propylamino, and the like.

"Alkoxy" means a —OR radical where R is alkyl as defined above, e.g., methoxy, ethoxy, propoxy, or 2-propoxy, n-, iso-, or tert-butoxy, and the like.

"Alkoxycarbonyl" means a —C(O)OR radical where R is alkyl as defined above, e.g., methoxycarbonyl, ethoxycarbonyl, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxyethyl, 1-, 2-, or 3-methoxypropyl, 2-ethoxyethyl, and the like.

"Alkoxyalkyloxy" or "alkoxyalkoxy" means a —OR radical where R is alkoxyalkyl as defined above, e.g., methoxyethoxy, 2-ethoxyethoxy, and the like.

"Aminoalkyl" means a linear monovalent hydrocarbon radical of one to six carbon atoms or a branched monovalent hydrocarbon radical of three to six carbons substituted with at least one, preferably one or two, —NRR' where R is hydrogen, alkyl, or —COR$^a$ where R$^a$ is alkyl, each as defined above, and R$^1$ is selected from hydrogen, alkyl, hydroxyalkyl, alkoxyalkyl, aryl, aralkyl, heteroaryl, heteroaralkyl, or haloalkyl, each as defined herein, e.g., aminomethyl, methylaminoethyl, 2-ethylamino-2-methylethyl, 1,3-diaminopropyl, dimethylaminomethyl, diethylaminoethyl, acetylaminopropyl, and the like.

"Aminoalkoxy" means a —OR radical where R is aminoalkyl as defined above, e.g., 2-aminoethoxy, 2-dimethylaminopropoxy, and the like.

"Aminocarbonyl" means a —CONRR' radical where R is independently hydrogen, alkyl, hydroxyalkyl, alkoxyalkyl, or aminoalkyl, each as defined herein and R$^1$ is hydrogen, alkyl, cycloalkyl, cycloalkylalkyl, aryl, aralkyl, heteroaryl, heteroaralkyl, heterocyclyl, heterocyclylalkyl, hydroxyalkyl, alkoxyalkyl, or aminoalkyl, each as defined herein, e.g., —CONH$_2$, methylaminocarbonyl, 2-dimethylaminocarbonyl, and the like.

"Aminosulfonyl" means a —SO$_2$NRR' radical where R is independently hydrogen, alkyl, hydroxyalkyl, alkoxyalkyl, or aminoalkyl, each as defined herein and R$^1$ is hydrogen, alkyl, cycloalkyl, cycloalkylalkyl, aryl, aralkyl, heteroaryl, heteroaralkyl, heterocyclyl, heterocyclylalkyl, hydroxyalkyl, alkoxyalkyl, or aminoalkyl, each as defined herein, e.g., —SO$_2$NH$_2$, methylaminosulfonyl, 2-dimethylaminosulfonyl, and the like.

"Acyl" means a —COR radical where R is alkyl, haloalkyl, cycloalkyl, cycloalkylalkyl, aryl, aralkyl, heteroaryl, heteroaralkyl, heterocyclyl, or heterocyclylalkyl, each as defined herein, e.g., acetyl, propionyl, benzoyl, pyridinylcarbonyl, and the like. When R is alkyl, the radical is also referred to herein as alkylcarbonyl.

"Acylamino" means a —NHCOR radical where R is alkyl, haloalkyl, cycloalkyl, cycloalkylalkyl, aryl, aralkyl, heteroaryl, heteroaralkyl, heterocyclyl, or heterocyclylalkyl, each as defined herein, e.g., acetylamino, propionylamino, and the like.

"Aryl" means a monovalent monocyclic or bicyclic aromatic hydrocarbon radical of 6 to 10 ring atoms e.g., phenyl or naphthyl.

"Aralkyl" means a -(alkylene)-R radical where R is aryl as defined above.

"Cycloalkyl" means a cyclic saturated monovalent hydrocarbon radical of three to ten carbon atoms, e.g., cyclopropyl, cyclobutyl, cyclopentyl, or cyclohexyl, and the like.

"Cycloalkylalkyl" means a -(alkylene)-R radical where R is cycloalkyl as defined above; e.g., cyclopropylmethyl, cyclobutylmethyl, cyclopentylethyl, or cyclohexylmethyl, and the like.

"Carboxy" means —COOH.

"Disubstituted amino" means a —NRR' radical where R and R' are independently alkyl, cycloalkyl, cycloalkylalkyl, acyl, sulfonyl, aryl, aralkyl, heteroaryl, heteroaralkyl, heterocyclyl, heterocyclylalkyl, hydroxyalkyl, alkoxyalkyl, or aminoalkyl, each as defined herein, e.g., dimethylamino, phenylmethylamino, and the like.

"Halo" means fluoro, chloro, bromo, or iodo, preferably fluoro or chloro.

"Haloalkyl" means alkyl radical as defined above, which is substituted with one or more halogen atoms, preferably one to five halogen atoms, preferably fluorine or chlorine, including those substituted with different halogens, e.g., —CH$_2$Cl, —CF$_3$, —CHF$_2$, —CH$_2$CF$_3$, —CF$_2$CF$_3$, and the like. When the alkyl is substituted with only fluoro, it is also referred to in this application as fluoroalkyl.

"Haloalkoxy" means a —OR radical where R is haloalkyl as defined above e.g., —OCF$_3$, —OCHF$_2$, and the like. When R is haloalkyl where the alkyl is substituted with only fluoro, it is also referred to in this application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Hydroxyalkoxy" or "hydroxyalkyloxy" means a —OR radical where R is hydroxyalkyl as defined above.

"Heterocyclyl" means a saturated or unsaturated monovalent monocyclic group of 5 to 8 ring atoms in which one or two ring atoms are heteroatom selected from N, O, or S(O)$_n$, where n is an integer from 0 to 2, the remaining ring atoms being C. The heterocyclyl ring is optionally fused to a (one) aryl or heteroaryl ring as defined herein provided the aryl and heteroaryl rings are monocyclic. The heterocyclyl ring fused to monocyclic aryl or heteroaryl ring is also referred to in this application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds provided that the ring is not aromatic. When the heterocyclyl group contains at least one nitrogen atom, it is also referred to herein as heterocycloamino and is a subset of the heterocyclyl group. When the heterocyclyl group is a saturated ring and is not fused to aryl or heteroaryl ring as stated above, it is also referred to herein as saturated monocyclic heterocyclyl.

"Heterocyclylalkyl" means a -(alkylene)-R radical where R is heterocyclyl ring as defined above e.g., tetraydrofuranylmethyl, piperazinylmethyl, morpholinylethyl, and the like.

"Heteroaryl" means a monovalent monocyclic or bicyclic aromatic radical of 5 to 10 ring atoms where one or more, preferably one, two, or three, ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like.

"Heteroaralkyl" means a -(alkylene)-R radical where R is heteroaryl as defined above.

"Monosubstituted amino" means a —NHR radical where R is alkyl, cycloalkyl, cycloalkylalkyl, acyl, sulfonyl, aryl, aralkyl, heteroaryl, heteroaralkyl, heterocyclyl, heterocyclylalkyl, hydroxyalkyl, alkoxyalkyl, or aminoalkyl, each as defined herein, e.g., methylamino, 2-phenylamino, hydroxyethylamino, and the like.

The present invention also includes the prodrugs of compounds of Formula (I). The term prodrug is intended to represent covalently bonded carriers, which are capable of releasing the active ingredient of Formula (I) when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups in vivo or by routine manipulation. Prodrugs of compounds of Formula (I) include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (I)), amides (e.g., trifluoroacetylamino, acetylamino, and the like), and the like. Prodrugs of compounds of Formula (I) are also within the scope of this invention.

The present invention also includes protected derivatives of compounds of Formula (I). For example, when compounds of Formula (I) contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, John Wiley & Sons, Inc. (1999), the disclosure of which is incorporated herein by reference in its entirety. The protected derivatives of compounds of Formula (I) can be prepared by methods well known in the art.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference.

The compounds of the present invention may have asymmetric centers. Compounds of the present invention containing an asymmetrically substituted atom may be isolated in optically active or racemic forms. It is well known in the art how to prepare optically active forms, such as by resolution of materials. All chiral, diastereomeric, racemic forms are within the scope of this invention, unless the specific stereochemistry or isomeric form is specifically indicated.

Certain compounds of Formula (I) can exist as tautomers and/or geometric isomers. All possible tautomers and cis and trans isomers, as individual forms and mixtures thereof are within the scope of this invention. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all polymorphic forms and hydrates of a compound of Formula (I) are within the scope of this invention.

"Oxo" or "carbonyl" means =(O) group.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Sulfonyl" means a —SO$_2$R radical where R is alkyl, haloalkyl, aryl, aralkyl, heteroaryl, heteroaralkyl, heterocyclyl, or heterocyclylalkyl, each as defined herein, e.g., methylsulfonyl, phenylsulfonyl, benzylsulfonyl, pyridinylsulfonyl, and the like.

The phrase in the definition of groups $Ar^1$ and $Ar^2$ in the claims and in the specification of this application " . . . wherein the aforementioned rings are optionally substituted with $R^a$, $R^b$, or $R^c$ independently selected from . . . " and similar phrases used for others groups in the claims and in the specification with respect to the compound of Formula (I) means that the rings can be mono-, di-, or trisubstituted unless indicated otherwise.

"Treating" or "treatment" of a disease includes:

preventing the disease, i.e. causing the clinical symptoms of the disease not to develop in a mammal that may be exposed to or predisposed to the disease but does not yet experience or display symptoms of the disease;

inhibiting the disease, i.e., arresting or reducing the development of the disease or its clinical symptoms; or relieving the disease, i.e., causing regression of the disease or its clinical symptoms.

A "therapeutically effective amount" means the amount of a compound of Formula (I) that, when administered to a mammal for treating a disease, is sufficient to effect such treatment for the disease. The "therapeutically effective amount" will vary depending on the compound, the disease and its severity and the age, weight, etc., of the mammal to be treated.

Table 1 shows representative compounds of Formula (I) where $R^1$, $R^2$, $R^4$ are hydrogen and $R^3$ and $R^5$ are as shown below.

TABLE 1

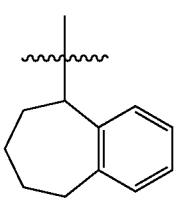

| Cpd # | X | R³ | R⁵ | Stereo-chem. at *C | Name | MS (ESI, pos. ion) m/z: (M + 1). |
|---|---|---|---|---|---|---|
| 1 | N | —CH₃ | 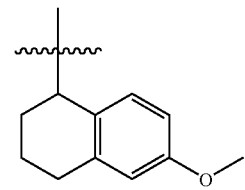 | R | 2-((R)-2-methyl-4-(6,7,8,9-tetrahydro-5H-benzo[7]annulen-5-yl)-piperazin-1-yl)acetic acid | 303.2 |
| 2 | N | —CH₃ | 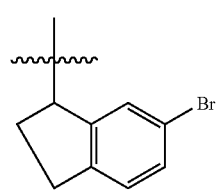 | R | 2-((R)-4-(6-methoxy-1,2,3,4-tetrahydro-naphthalen-1-yl)-2-methylpiperazin-1-yl)acetic acid | 319.2 |
| 3 | N | —CH₃ | 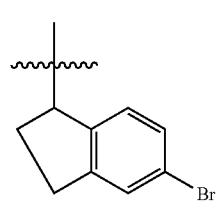 | R | 2-((R)-4-(6-bromo-2,3-dihydro-1H-inden-1-yl)-2-methyl-piperazin-1-yl)acetic acid | 353.0 |
| 4 | N | —CH₃ | 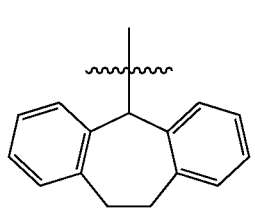 | R | 2-((R)-4-(5-bromo-2,3-dihydro-1H-inden-1-yl)-2-methyl-piperazin-1-yl)acetic acid | 353.0 |
| 5 | N | —CH₃ | 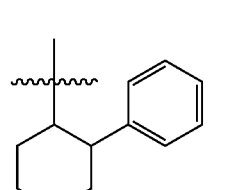 | R | | 351.1 |
| 6 | N | —CH₃ |  | R | 2-((R)-2-methyl-4-(2-phenylcyclohexyl)-piperazin-1-yl)acetic acid dihydrochloride | 317.2 |

TABLE 1-continued

| Cpd # | X | R³ | R⁵ | Stereo-chem. at *C | Name | MS (ESI, pos. ion) m/z: (M + 1) |
|---|---|---|---|---|---|---|
| 7 | —CH— | H | phenyl(3-(trifluoromethyl)phenyl)amino | | 2-(4-(phenyl(3-(trifluoromethyl)-phenyl)amino)piperidin-1-yl)-acetic acid | 379.1 |
| 8 | —CH— | H | benzhydryl | | 2-(4-benzhydrylpiperidin-1-yl)acetic acid | 310.2 |
| 9 | N | H | naphth-1-yl | | 2-(4-naphth-1-ylpiperazin-1-yl)acetic acid | 271.1 |
| 10 | N | —CH₃ | naphth-1-yl | R | (R)-2-(2-methyl-4-naphth-1-ylpiperazin-1-yl)acetic acid | 285.1 |
| 11 | N | H | anthracen-9-yl | | 2-(4-anthracen-9-ylpiperazin-1-yl)acetic acid | 321.2 |
| 12 | N | —CH₃ | anthracen-9-yl | R | (R)-2-(4-anthracen-9-yl-2-methyl-piperazin-1-yl)acetic acid | 335.1 |
| 13 | N | H | 1-phenylcyclohexyl | | 2-(4-(1-phenylcyclohexyl)piperazin-1-yl)acetic acid | 303.1 |
| 14 | N | —CH₃ | 1-phenylcyclohexyl | R | (R)-2-(2-methyl-4-(1-phenyl-cyclohexyl)-piperazin-1-yl)acetic acid | 317.1 |
| 15 | —CH— | —CH₃ | benzhydryl | RS | 2-(4-benzhydryl-2-methyl-piperidin-1-yl)acetic acid | 324.2 |
| 16 | —CH— | H | phenyl(2-(trifluoromethyl)phenyl)methyl | | 2-(4-(phenyl(2-(trifluoromethyl)-phenyl)-methyl)piperidin-1-yl)acetic acid | 378.1 |

TABLE 1-continued

| Cpd # | X | R³ | R⁵ | Stereo-chem. at *C | Name | MS (ESI, pos. ion) m/z: (M + 1). |
|---|---|---|---|---|---|---|
| 17 | —CH— | H | 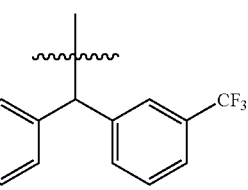 | | 2-(4-(phenyl(3-(trifluoromethyl)phenyl)-methyl)piperidin-1-yl)acetic acid | 378.1 |
| 18 | —CH— | H | 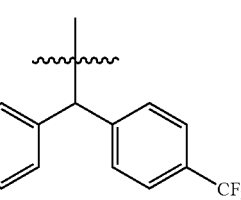 | | 2-(4-(phenyl(4-(trifluoromethyl)phenyl)-methyl)piperidin-1-yl)acetic acid | 378.1 |
| 19 | —CH— | —CH₃ | 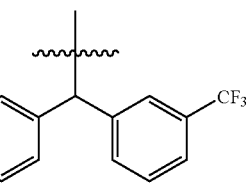 | RS | 2-(2-methyl-4-(phenyl(3-(trifluoro-methyl)phenyl)methyl)-piperidin-1-yl)acetic acid | 392.1 |
| 20 | —CH— | —CH₃ | 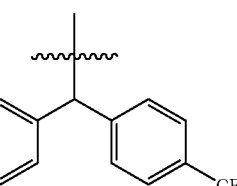 | RS | 2-(2-methyl-4-(phenyl(4-(trifluoro-methyl)phenyl)methyl)-piperidin-1-yl)acetic acid | 392.1 |
| 21 | —CH— | —CH₃ | 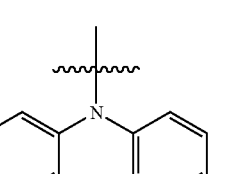 | RS | 2-(4-(diphenylamino)-2-methylpiperidin-1-yl)acetic acid | 325.1 |
| 22 | —CH— | H | 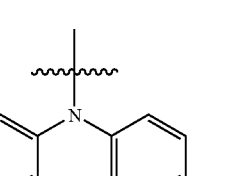 | | 2-(4-(phenyl(4-(trifluoromethyl)phenyl)-amino)piperidin-1-yl)acetic acid | 379.1 |

TABLE 1-continued

| Cpd # | X | R³ | R⁵ | Stereochem. at *C | Name | MS (ESI, pos. ion) m/z: (M + 1) |
|---|---|---|---|---|---|---|
| 23 | —CH— | —CH₃ | N,N-diphenyl-4-(trifluoromethyl)aniline linker | RS | 2-(2-methyl-4-(phenyl(4-(trifluoro-methyl)phenyl)amino)-piperidin-1-yl)acetic acid | 393.2 |
| 24 | —CH— | —CH₃ | N,N-diphenyl-3-(trifluoromethyl)aniline linker | RS | 2-(2-methyl-4-(phenyl(3-(trifluoro-methyl)phenyl)amino)-piperidin-1-yl)acetic acid | 393.1 |
| 25 | N | —CH₃ | 1-(3-(trifluoromethyl)phenyl)cyclohexyl | R | (R)-2-(2-methyl-4-(1-(3-(trifluoro-methyl)phenyl)cyclohexyl)-piperazin-1-yl)acetic acid | 385.1 |
| 26 | N | —CH₃ | 1-(4-chlorophenyl)cyclohexyl | R | (R)-2-(4-(1-(4-chlorophenyl)cyclohexyl)-2-methylpiperazin-1-yl)acetic acid | 251.17 |
| 27 | CH | H | N,N-diphenylamino | | 2-(4-(diphenylamino)piperidin-1-yl)acetic acid | 311.27 |
| 28 | CH | H | 9H-fluoren-9-yl | | 2-(4-(9H-fluoren-9-yl)piperidin-1-yl)acetic acid | 308.17 |
| 29 | CH | H | napth-1-yl | | 2-(4-naphth-1-ylpiperidin-1-yl)acetic acid | 270.16 |
| 30 | CH | H | 9H-xanthen-9-yl | | 2-(4-(9H-xanthen-9-yl)piperidin-1-yl)acetic acid | 324.10 |

Table 2 shows representative compounds of Formula (I) where $R^1$, $R^2$, $R^3$ and $R^4$ are hydrogen, n1 is 0 and n2, $R^3$ and $R^5$ are as shown below.

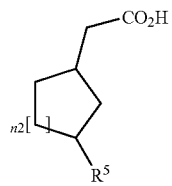

| Cpd # | n2 | R5 | Name | MS (ESI, pos. ion) m/z: (M + 1) |
|---|---|---|---|---|
| 1 | 2 | phenyl(4-(trifluoromethyl)-phenyl)methyl | 2-(3-(phenyl(4-(trifluoromethyl)-phenyl)methyl) piperidin-1-yl)acetic acid | 378.1 |
| 2 | 2 | phenyl(3-(trifluoromethyl)-phenyl)methyl | 2-(3-(phenyl(3-(trifluoromethyl)-phenyl)methyl) piperidin-1-yl)acetic acid | 378.1 |
| 3 | 2 | phenyl(4-(trifluoromethyl)-phenyl)amino | 2-(3-(phenyl(4-(trifluoromethyl)-phenyl)amino) piperidin-1-yl)acetic acid | 379.2 |
| 4 | 2 | phenyl(3-(trifluoromethyl)-phenyl)amino | 2-(3-(phenyl(3-(trifluoromethyl)-phenyl)amino) piperidin-1-yl)acetic acid | 379.1 |
| 5 | 1 | phenyl(4-(trifluoromethyl)-phenyl)amino | 2-(3-(phenyl(4-(trifluoromethyl)-phenyl)amino) pyrrolidin-1-yl)acetic acid | 365.1 |
| 6 | 1 | phenyl(4-(trifluoromethyl)-phenyl)methyl | 2-(3-(phenyl(4-(trifluoromethyl)-phenyl) methyl)pyrrolidin-1-yl)acetic aci | 364.1 |

-continued

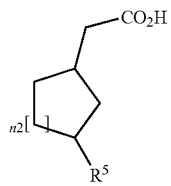

| Cpd # | n2 | R5 | Name | MS (ESI, pos. ion) m/z: (M + 1). |
|---|---|---|---|---|
| 7 | 1 | (phenyl)(m-tolyl)methyl | 2-(3-(phenyl(m-tolyl)methyl)-pyrrolidin-1-yl)acetic acid | 310.5 |
| 8 | 1 | N,N-diphenylamino | 2-(3-(diphenylamino)-pyrrolidin-1-yl)acetic acid | 297.1 |
| 9 | 1 | (3-bromophenyl)(phenyl)amino | 2-(3-((3-bromophenyl)(phenyl)-amino)pyrrolidin-1-yl)acetic acid | 375.12 |
| 10 | 1 | phenyl(3-(pyridin-3-yl)phenyl)amino | 2-(3-(phenyl(3-(pyridin-3-yl)-phenyl)amino)pyrrolidin-1-yl)acetic acid | 374.19 |
| 11 | 1 | phenyl(3-(thien-4-yl)phenyl)amino | 2-(3-(phenyl(3-(thien-4-yl)-phenyl)amino)pyrrolidin-1-yl)acetic acid | 380.1 |
| 12 | 1 | (4-fluorophenyl)(4-(pyridin-3-yl)phenyl)amino | 2-(3-(4-fluorophenyl(4-(pyridin-3-yl)-phenyl)amino)pyrrolidin-1-yl)acetic acid | 374.19 |

-continued

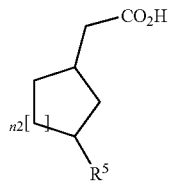

|Cpd #|n2|R5|Name|MS (ESI, pos. ion) m/z: (M + 1).|
|---|---|---|---|---|
|13|1|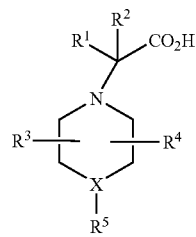|2-(3-(phenyl(3-(pyridin-2-yl)-phenyl)amino) pyrrolidin-1-yl)acetic acid|374.19|
|14|1|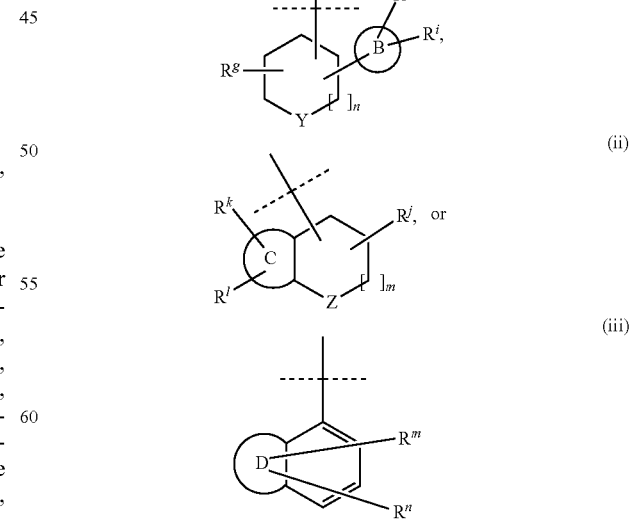|2-(3-((4-bromophenyl)(4-fluorophenyl)amino) pyrrolidin-1-yl)acetic acid|392.99|

Embodiments (IA) In one embodiment, the compound for Formula (I) is represented by the formula:

(I)

wherein:

X is —CH— or —N—;

$R^1$ and $R^2$ are independently hydrogen or alkyl;

$R^3$ and $R^4$ are independently hydrogen, alkyl, haloalkyl, alkoxy, or haloalkoxy; and $R^5$ is:

(a) —$NAr^1Ar^2$ or —$CHAr^1Ar^2$ when X is —CH—; where $Ar^1$ and $Ar^2$ are independently aryl, heteroaryl, cycloalkyl, or heterocyclyl where each of the aforementioned ring is optionally substituted with $R^a$, $R^b$ or $R^c$ where $R^a$ is alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and $R^b$ and $R^c$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring in $R^a$, $R^b$ and $R^c$ is optionally substituted with $R^d$, $R^e$ or $R^f$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino; or (b) a ring of formula (i), (ii), or (iii):

(i)

(ii)

(iii)

where:

n and m are independently 0-2;

ring B, C, or D is phenyl or a 5- to 6-membered heteroaryl ring;

Y and Z are independently —CH$_2$—, —O—, —NH—, —S— —SO—, or —SO$_2$—; and two of R$^g$, R$^h$, R$^i$, R$^j$, R$^k$, R$^l$, R$^m$ and R$^n$ are independently hydrogen, alkyl, halo, haloalkyl, haloalkoxy, alkylthio, cyano, alkoxy, amino, monosubstituted amino, disubstituted amino, acyl, carboxy, or alkoxycarbonyl and the third of R$^g$, R$^h$, R$^i$, R$^j$, R$^k$, R$^l$, R$^m$ and R$^n$ is hydrogen, alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring in R$^g$, R$^h$, R$^i$, R$^j$, R$^k$, R$^l$, R$^m$ and R$^n$ is optionally substituted with R$^o$, R$^p$ and R$^q$ which are independently alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino; or (c) a ring of formula (iv), (v), (vi), (vii), (viii), or (ix):

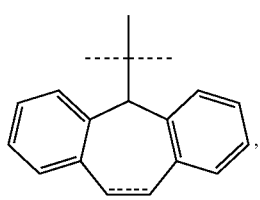
(iv)

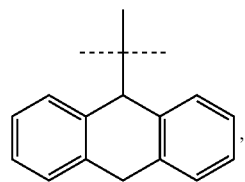
(v)

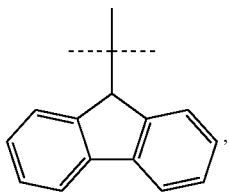
(vi)

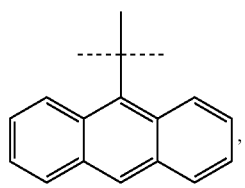
(vii)

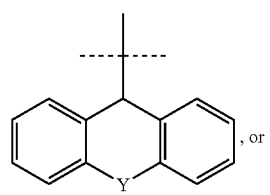
(viii), or

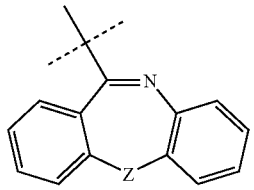
(ix)

where:

Y and Z are independently —CH$_2$—, —O—, —NH—, —S— —SO—, or —SO$_2$—; and ring (iv), (v), (vi), (vii), (viii), and (ix) are independently substituted with R$^r$, R$^s$ and R$^t$ where R$^r$ and R$^s$ are independently hydrogen, alkyl, halo, haloalkyl, haloalkoxy, alkylthio, cyano, alkoxy, amino, monosubstituted amino, disubstituted amino, acyl, carboxy, or alkoxycarbonyl and R$^t$ is hydrogen, alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring in R$^r$, R$^s$ and R$^t$ is optionally substituted with R$^u$, R$^v$ or R$^w$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino; or a pharmaceutically acceptable salt thereof provided that: the compound of Formula (I) is not 2-(4-benzhydrylpiperidin-1-yl)acetic acid; 2-(4-(naphthalen-1-yl)piperazin-1-yl)acetic acid;

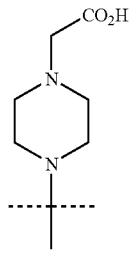

where R$^5$ is a ring of formula:

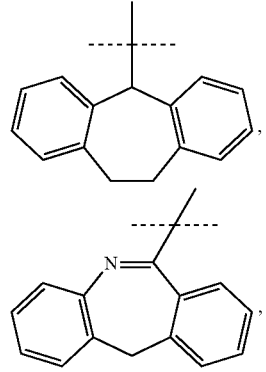

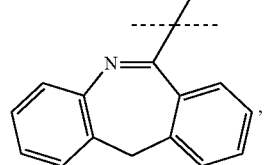

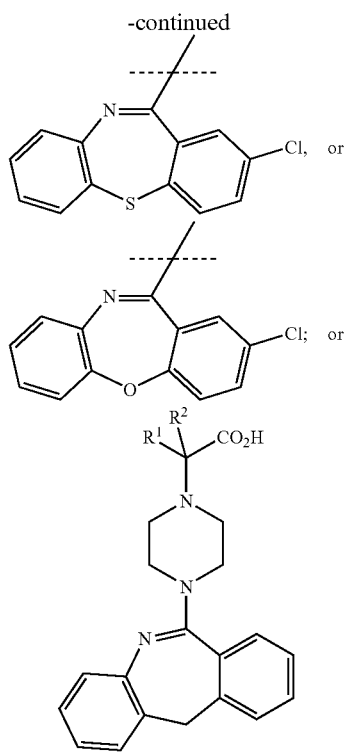

where $R^1$ is hydrogen and $R^2$ is methyl or $R^1$ and $R^2$ are methyl.

(I) Within embodiment (IA), in one embodiment the compound of Formula (I) is represented by the formula:

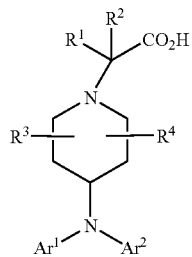

where the groups are as defined in (IA) above.
Within embodiment (I):
  (i) In one group of compounds, $R^1$ and $R^2$ are hydrogen.
  (ii) In another group of compounds, $R^1$ is hydrogen and $R^2$ is alkyl.
  (iii) In yet another group of compounds, $R^1$ is hydrogen and $R^2$ is methyl.
  (A) Within embodiment (I) and groups (i)-(iii), in one group of compounds, $R^3$ and $R^4$ are hydrogen.
  (B) Within embodiment (I) and groups (i)-(iii), another group of compounds is that wherein $R^3$ is hydrogen and $R^4$ is methyl, ethyl, or propyl and is located at the carbon atom that is ortho to the piperidine nitrogen atom i.e., nitrogen in the piperidine ring. Within this group (B), one group of compounds is that wherein $R^4$ is methyl. Within this group (B), another group of compounds is that wherein $R^4$ is methyl and the stereochemistry at the carbon atom carrying the $R^4$ group is (R). Within this group, yet another group of compounds is that wherein $R^4$ is methyl and the stereochemistry at the carbon atom carrying the $R^4$ group is (S).

(a) Within embodiment (I), groups (i)-(iii), (A), (B) and groups contained therein, and groups formed as a result of combination of groups (i)-(iii), (A), (B), and groups contained therein, one group of compounds is that wherein $Ar^1$ and $Ar^2$ are phenyl, each phenyl optionally substituted as defined in (IA) above.
    Within group (a), one group of compounds is that wherein $Ar^1$ and $Ar^2$ are phenyl.
    Within group (a), another group of compounds is that wherein $Ar^1$ is phenyl and $Ar^2$ is phenyl substituted with $R^a$ selected from alkyl, halo, haloalkyl, or haloalkoxy, preferably methyl, fluoro, chloro, trifluoromethyl, trifluoromethoxy or 2,2,2-trifluoroethoxy.
    Within group (a), another group of compounds is that wherein $Ar^1$ is phenyl and $Ar^2$ is phenyl substituted with $R^a$ selected from alkyl, halo, haloalkyl, or haloalkoxy, preferably methyl, fluoro, chloro, trifluoromethyl, trifluoromethoxy or 2,2,2-trifluoroethoxy and $R^a$ is located at the 2-, 3-, or 4-, preferably 3-position of the phenyl ring, the carbon atom attached to the —$NAr^1$ group being the 1-position.
    Within group (a), another group of compounds is that wherein $Ar^1$ is phenyl substituted with $R^a$ selected from alkyl, halo, haloalkyl, or haloalkoxy, preferably methyl, fluoro, chloro, trifluoromethyl, trifluoromethoxy or 2,2,2-trifluoroethoxy, preferably $R^a$ is located at the 3-position of the phenyl ring and $Ar^2$ is phenyl substituted with $R^b$ selected from alkyl, halo, haloalkyl, or haloalkoxy, preferably methyl, fluoro, chloro, trifluoromethyl, trifluoromethoxy or 2,2,2-trifluoroethoxy, preferably $R^b$ is located at the 2-, 3-, or 4-, preferably 3-position of the phenyl ring.
    Within group (a), another group of compounds is that wherein $Ar^1$ and $Ar^2$ are phenyl optionally substituted with $R^b$ or $R^c$ where $R^b$ and $R^c$ are independently alkyl, halo, haloalkyl, haloalkoxy, cyano, or five or six membered heterocycle or heteroaryl provided that at least one of the phenyl ring is substituted i.e., covers compounds where one of the phenyl ring is monosubstituted or disubstituted and the other is unsubstituted or both rings are monosubstituted.
    Within group (a), another group of compounds is that wherein $Ar^1$ is phenyl and $Ar^2$ is phenyl substituted with $R^a$ selected from alkyl, halo, haloalkyl, haloalkoxy or phenyl, preferably methyl, fluoro, chloro, trifluoromethyl, trifluoromethoxy, phenyl, or 2,2,2-trifluoroethoxy and $R^a$ is located at the 2-, 3-, or 4-, preferably 3-position of the phenyl ring, the carbon atom attached to the —$NAr^1$ group being the 1-position.
  (b) Within embodiment (I), groups (i)-(iii), (A), (B) and groups contained therein, and groups formed as a result of combination of groups (i)-(iii), (A), (B), and groups contained therein, another group of compounds is that wherein $Ar^1$ is phenyl and $Ar^2$ is heteroaryl, each optionally substituted as defined in (IA) above.
    Within group (b), one group of compounds is that wherein $Ar^1$ is phenyl and $Ar^2$ is heteroaryl, preferably pyridinyl, pyrimidinyl, pyridazinyl, pyrazinyl, or thienyl, each $Ar^1$ and $Ar^2$ optionally substituted as defined in (IA) above. Preferably, $Ar^1$ and $Ar^2$ are independently optionally substituted with $R^b$ or $R^c$ where $R^b$ and $R^c$ are independently alkyl, halo, haloalkyl, haloalkoxy, cyano, or five or six membered heterocycle or heteroaryl provided that at least one of $Ar^1$ and $Ar^2$ is substituted i.e., covers compounds where one of the phenyl or heteroaryl ring is mono or disubstituted and the other is unsubstituted or both rings are monosubstituted.
    Within group (b), another group of compounds is that wherein $Ar^1$ is phenyl and $Ar^2$ is pyridinyl, pyrimidinyl, pyridazinyl, pyrazinyl, or thienyl optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy.

Within group (b), another group of compounds is that wherein $Ar^1$ is phenyl optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy and $Ar^2$ is pyridinyl, pyrimidinyl, pyridazinyl, pyrazinyl, or thienyl, preferably thienyl.

(c) Within embodiment (I), groups (i)-(iii), (A), (B) and groups contained therein, and groups formed as a result of combination of groups (i)-(iii), (A), (B), and groups contained therein, yet another group of compounds is that wherein $Ar^1$ and $Ar^2$ are heteroaryl optionally substituted as defined in (IA) above.

Within this embodiment (c), one group of compounds is that wherein $Ar^1$ and $Ar^2$ are heteroaryl each optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy.

(d) Within embodiment (I), groups (i)-(iii), (A), (B) and groups contained therein, and groups formed as a result of combination of groups (i)-(iii), (A), (B), and groups contained therein, yet another group of compounds is that wherein $Ar^1$ is phenyl and $Ar^2$ is heterocyclyl, each $Ar^1$ and $Ar^2$ optionally substituted as in (IA) above.

Within this embodiment (d), one group of compounds is that wherein $Ar^1$ is phenyl and $Ar^2$ is tetrahydropyranyl, piperidinyl, or tetrahydrofuranyl, each $Ar^1$ and $Ar^2$ optionally substituted as in (IA) above.

Within this embodiment (d), one group of compounds is that wherein $Ar^1$ is phenyl and $Ar^2$ is heterocyclyl, preferably tetrahydropyranyl, piperidinyl, or tetrahydrofuranyl, optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy. Within this group, another group of compounds is that wherein $Ar^1$ is phenyl optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy and $Ar^2$ is tetrahydropyranyl, piperidinyl, or tetrahydrofuranyl.

(e) Within embodiment (I), groups (i)-(iii), (A), (B) and groups contained therein, and groups formed as a result of combination of groups (i)-(iii), (A), (B), and groups contained therein, yet another group of compounds is that wherein $Ar^1$ is phenyl and $Ar^2$ is cycloalkyl, each $Ar^1$ and $Ar^2$ optionally substituted as defined above.

Within this embodiment (e), one group of compounds is that wherein $Ar^1$ is phenyl and $Ar^2$ is cyclopentyl or cyclohexyl, each $Ar^1$ and $Ar^2$ optionally substituted as defined above.

Within this embodiment (e), one group of compounds is that wherein $Ar^1$ is phenyl and $Ar^2$ is cycloalkyl, preferably cyclopentyl or cyclohexyl, each $Ar^1$ and $Ar^2$ optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy.

Within this embodiment (e), one group of compounds is that wherein $Ar^1$ is phenyl and $Ar^2$ is cyclopropyl, $Ar^1$ optionally substituted as defined above.

Within this embodiment (e), one group of compounds is that wherein $Ar^1$ is phenyl and $Ar^2$ is cyclopropyl, $Ar^1$ optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy.

(f) Within embodiment (I), groups (i)-(iii), (A), (B) and groups contained therein, and groups formed as a result of combination of groups (i)-(iii), (A), (B), and groups contained therein, yet another group of compounds is that wherein $Ar^1$ and $Ar^2$ are heteroaryl optionally substituted as defined above.

Within this embodiment (f), one group of compounds is that wherein $Ar^1$ and $Ar^2$ are heteroaryl each optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy.

(g) Within embodiment (I), groups (i)-(iii), (A), (B) and groups contained therein, and groups formed as a result of combination of groups (i)-(iii), (A), (B), and groups contained therein, yet another group of compounds is that wherein $Ar^1$ is heteroaryl and $Ar^2$ is cycloalkyl each $Ar^1$ and $Ar^2$ optionally substituted as defined above.

(h) Within embodiment (I), groups (i)-(iii), (A), (B) and groups contained therein, and groups formed as a result of combination of groups (i)-(iii), (A), (B), and groups contained therein, yet another group of compounds is that wherein $Ar^1$ is heterocyclyl and $Ar^2$ is heteroaryl each $Ar^1$ and $Ar^2$ optionally substituted as defined above.

(i) Within embodiment (I), groups (i)-(iii), (A), (B) and groups contained therein, and groups formed as a result of combination of groups (i)-(iii), (A), (B), and groups contained therein, yet another group of compounds is that wherein $Ar^1$ is cycloalkyl and $Ar^2$ is heterocyclyl each $Ar^1$ and $Ar^2$ optionally substituted as defined above.

(j) Within embodiment (I), groups (i)-(iii), (A), (B) and groups contained therein, and groups formed as a result of combination of groups (i)-(iii), (A), (B), and groups contained therein, yet another group of compounds is that wherein $Ar^1$ is cycloalkyl and $Ar^2$ is cycloalkyl each $Ar^1$ and $Ar^2$ optionally substituted as defined above.

(II). Within embodiment (IA), in another embodiment, the compound of Formula (I) is represented by the formula:

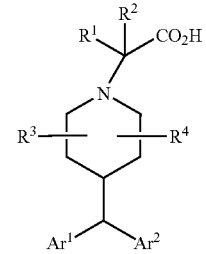

where the groups are as defined in (IA) above.

Within this embodiment (II):
(i) In one group of compounds, $R^1$ and $R^2$ are hydrogen.
(ii) In another group of compounds, $R^1$ is hydrogen and $R^2$ is alkyl.
(iii) In yet another group of compounds, $R^1$ is hydrogen and $R^2$ is methyl.

(A) Within embodiment (II) and groups (i)-(iii), in one group of compounds, $R^3$ and $R^4$ are hydrogen.
(B) Within embodiment (II) and groups (i)-(iii), another group of compounds is that wherein $R^3$ is hydrogen and $R^4$ is methyl, ethyl, or propyl and is located at the carbon atom that is ortho to the piperidine nitrogen atom i.e., nitrogen in the piperidine ring. Within group (B), one group of compounds is that wherein $R^4$ is methyl. Within group (B), another group of compounds is that wherein $R^4$ is methyl and the stereochemistry at the carbon atom carrying the $R^4$ group is (R). Within this group, yet another group of compounds is that wherein $R^4$ is methyl and the stereochemistry at the carbon atom carrying the $R^4$ group is (S).

(a) Within embodiment (II), groups (i)-(iii), (A), (B) and groups contained therein, and groups formed as a result of combination of groups (i)-(iii), (A), (B), and groups contained therein, one group of compounds is that wherein $Ar^1$ and $Ar^2$ are phenyl, each phenyl optionally substituted as defined in (IA) above.

Within group (a), one group of compounds is that wherein $Ar^1$ and $Ar^2$ are phenyl. Within this embodiment, another group of compounds is that wherein $Ar^1$ is phenyl and $Ar^2$ is phenyl substituted with $R^a$ is alkyl, halo, haloalkyl, or haloalkoxy, preferably methyl, fluoro, chloro, trifluoromethyl, trifluoromethoxy or 2,2,2-trifluoroethoxy.

Within group (a), another group of compounds is that wherein $Ar^1$ is phenyl and $Ar^2$ is phenyl substituted with $R^a$ is alkyl, halo, haloalkyl, or haloalkoxy, preferably methyl, fluoro, chloro, trifluoromethyl, trifluoromethoxy or 2,2,2-trifluoroethoxy and $R^a$ is located at the 2-, 3-, or 4-, preferably 3-position of the phenyl ring, the carbon atom attached to the —$CHAr^1$ group being the 1-position.

Within group (a), another group of compounds is that wherein $Ar^1$ is phenyl substituted with $R^a$ selected from alkyl, halo, haloalkyl, or haloalkoxy, preferably methyl, fluoro, chloro, trifluoromethyl, trifluoromethoxy or 2,2,2-trifluoroethoxy, preferably $R^a$ is located at the 2-, 3-, or 4-, preferably 3-position of the phenyl ring and $Ar^2$ is phenyl substituted with $R^b$ selected from alkyl, halo, haloalkyl, or haloalkoxy, preferably methyl, fluoro, chloro, triflu 2-, 3-, or 4-, preferably 3-position of the phenyl ring.

Within group (a), another group of compounds is that wherein $Ar^1$ and $Ar^2$ are phenyl independently optionally substituted with $R^b$ or $R^c$ where $R^b$ and $R^c$ are independently alkyl, halo, haloalkyl, haloalkoxy, cyano, or five or six membered heterocycle or heteroaryl provided that at least one of the phenyl is substituted i.e., covers compounds where one of the phenyl ring is mono or disubstituted and the other is unsubstituted or both rings are monosubstituted.

Within group (a), another group of compounds is that wherein $Ar^1$ is phenyl and $Ar^2$ is phenyl substituted with $R^a$ selected from alkyl, halo, haloalkyl, haloalkoxy or phenyl, preferably methyl, fluoro, chloro, trifluoromethyl, trifluoromethoxy, phenyl, or 2,2,2-trifluoroethoxy and $R^a$ is located at the 2-, 3-, or 4-, preferably 3-position of the phenyl ring, the carbon atom attached to the —$NAr^2$ group being the 1-position.

(b) Within embodiment (II), groups (i)-(iii), (A), (B) and groups contained therein, and groups formed as a result of combination of groups (i)-(iii), (A), (B), and groups contained therein, another group of compounds is that wherein $Ar^1$ is phenyl and $Ar^2$ is heteroaryl, each optionally substituted as defined in (IA) above.

Within group (b), one group of compounds is that wherein $Ar^1$ is phenyl and $Ar^2$ is heteroaryl, preferably pyridinyl, pyrimidinyl, pyridazinyl, pyrazinyl, or thienyl, each $Ar^1$ and $Ar^2$ optionally substituted as defined in (IA) above. Preferably, $Ar^1$ and $Ar^2$ are independently optionally substituted with $R^b$ or $R^c$ where $R^b$ and $R^c$ are independently alkyl, halo, haloalkyl, haloalkoxy, cyano, or five or six membered heterocycle or heteroaryl provided that at least one of $Ar^1$ and $Ar^2$ is substituted i.e., covers compounds where one of the phenyl or heteroaryl ring is mono or disubstituted and the other is unsubstituted or both rings are monosubstituted.

Within group (b), another group of compounds is that wherein $Ar^1$ is phenyl and $Ar^2$ is pyridinyl, pyrimidinyl, pyridazinyl, pyrazinyl, or thienyl optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy.

Within group (b), another group of compounds is that wherein $Ar^1$ is phenyl optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy and $Ar^2$ is pyridinyl, pyrimidinyl, pyridazinyl, pyrazinyl, or thienyl, preferably thienyl.

(c) Within embodiment (II), groups (i)-(iii), (A), (B) and groups contained therein, and groups formed as a result of combination of groups (i)-(iii), (A), (B), and groups contained therein, yet another group of compounds is that wherein $Ar^1$ and $Ar^2$ are heteroaryl optionally substituted as defined in (IA) above.

Within group (c), one group of compounds is that wherein $Ar^1$ and $Ar^2$ are heteroaryl each optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy.

(d) Within embodiment (II), groups (i)-(iii), (A), (B) and groups contained therein, and groups formed as a result of combination of groups (i)-(iii), (A), (B), and groups contained therein, yet another group of compounds is that wherein $Ar^1$ is phenyl and $Ar^2$ is heterocyclyl, each $Ar^1$ and $Ar^2$ optionally substituted as defined in (IA) above.

Within this embodiment (d), one group of compounds is that wherein $Ar^1$ is phenyl and $Ar^2$ is tetrahydropyranyl, piperidinyl, or tetrahydrofuranyl, each $Ar^1$ and $Ar^2$ optionally substituted as defined in (IA) above.

Within this embodiment (d), one group of compounds is that wherein $Ar^1$ is phenyl and $Ar^2$ is heterocyclyl, preferably tetrahydropyranyl, piperidinyl, or tetrahydrofuranyl optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy. Within this group, another group of compounds is that wherein $Ar^1$ is phenyl optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy and $Ar^2$ is tetrahydropyranyl, piperidinyl, or tetrahydrofuranyl.

(e) Within embodiment (II), groups (i)-(iii), (A), (B) and groups contained therein, and groups formed as a result of combination of groups (i)-(iii), (A), (B), and groups contained therein, yet another group of compounds is that wherein $Ar^1$ is phenyl and $Ar^2$ is cycloalkyl, each $Ar^1$ and $Ar^2$ optionally substituted as defined above.

Within this embodiment (e), one group of compounds is that wherein $Ar^1$ is phenyl and $Ar^2$ is cyclobutyl, cyclopentyl or cyclohexyl, each $Ar^1$ and $Ar^2$ optionally substituted as defined above.

Within this embodiment (e), one group of compounds is that wherein $Ar^1$ is phenyl and $Ar^2$ is cycloalkyl, preferably cyclobutyl, cyclopentyl or cyclohexyl, each $Ar^1$ and $Ar^2$ optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy.

Within this embodiment (e), one group of compounds is that wherein $Ar^1$ is phenyl and $Ar^2$ is cyclopropyl, $Ar^1$ optionally substituted as defined above.

Within this embodiment (e), one group of compounds is that wherein $Ar^1$ is phenyl and $Ar^2$ is cyclopropyl, $Ar^1$ optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy.

(f) Within embodiment (II), groups (i)-(iii), (A), (B) and groups contained therein, and groups formed as a result of combination of groups (i)-(iii), (A), (B), and groups contained therein, yet another group of compounds is that wherein $Ar^1$ and $Ar^2$ are heteroaryl optionally substituted as defined above.

Within this embodiment (f), one group of compounds is that wherein $Ar^1$ and $Ar^2$ are heteroaryl each optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy.

(g) Within embodiment (II), groups (i)-(iii), (A), (B) and groups contained therein, and groups formed as a result of combination of groups (i)-(iii), (A), (B), and groups contained therein, yet another group of compounds is that wherein $Ar^1$ is heteroaryl and $Ar^2$ is cycloalkyl each $Ar^1$ and $Ar^2$ optionally substituted as defined above.

(h) Within embodiment (II), groups (i)-(iii), (A), (B) and groups contained therein, and groups formed as a result of combination of groups (i)-(iii), (A), (B), and groups contained therein, yet another group of compounds is that wherein $Ar^1$ is heterocyclyl and $Ar^2$ is heteroaryl each $Ar^1$ and $Ar^2$ optionally substituted as defined above.

(i) Within embodiment (II), groups (i)-(iii), (A), (B) and groups contained therein, and groups formed as a result of combination of groups (i)-(iii), (A), (B), and groups contained therein, yet another group of compounds is that wherein $Ar^1$ is cycloalkyl and $Ar^2$ is heterocyclyl each $Ar^1$ and $Ar^2$ optionally substituted as defined above.

(j) Within embodiment (II), groups (i)-(iii), (A), (B) and groups contained therein, and groups formed as a result of combination of groups (i)-(iii), (A), (B), and groups contained therein, yet another group of compounds is that wherein $Ar^1$ is cycloalkyl and $Ar^2$ is cycloalkyl each $Ar^1$ and $Ar^2$ optionally substituted as defined above.

(III). Within embodiment (IA), in another embodiment, the compound of Formula (I) is represented by the formula:

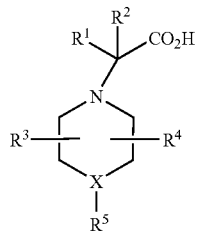

and $R^5$ is a ring of formula (i)-(iii).

Within embodiment (III):
  (A) In one embodiment, X is —CH—.
  (B) In another embodiment, X is —N—.
  (i) Within embodiments A and B, in one group of compounds, $R^1$ and $R^2$ are hydrogen.
  (ii) Within embodiments (III), A and B, in another group of compounds, $R^1$ is hydrogen and $R^2$ is alkyl.
  (iii) Within embodiments (III), A and B, in yet another group of compounds, $R^1$ is hydrogen and $R^2$ is methyl.

(a) Within embodiments (III), A, B, (i)-(iii), and groups formed by combination of A, B and (i)-(iii), in one group of compounds, $R^3$ and $R^4$ are hydrogen.

(b) Within embodiments (III), A, B, (i)-(iii), and groups formed by combination of A, B and (i)-(iii), another group of compounds is that wherein $R^3$ is hydrogen and $R^4$ is methyl, ethyl, or propyl and is located at the carbon atom that is ortho to the ring nitrogen atom substituted with —$CR^1R^2CO_2H$ group. Within this embodiment, one group of compounds is that wherein $R^4$ is methyl. Within this embodiment, one group of compounds is that wherein $R^4$ is methyl and the stereochemistry at the carbon atom carrying the $R^4$ group is (R). Within this embodiment, one group of compounds is that wherein $R^4$ is methyl and the stereochemistry at the carbon atom carrying the $R^4$ group is (S).

(c) Within the embodiments (III), A, B, (i)-(iii), (a), and (b) and groups contained therein, and groups formed as a result of combination of groups A, B, (i)-(iii), (a), (b), and groups contained therein, one group of compounds is that wherein $R^5$ is a ring of formula (i).

Within this embodiment (c), one group of compounds is that wherein $R^5$ is a ring of formula:

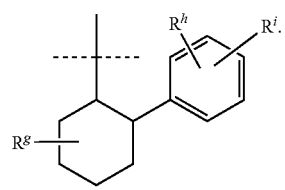

Within this embodiment (c), one group of compounds is that wherein $R^5$ is a ring of formula:

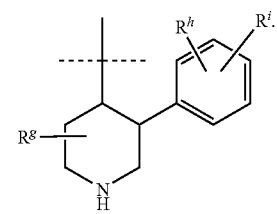

Within this embodiment (c), another group of compounds is that wherein A is a ring of formula:

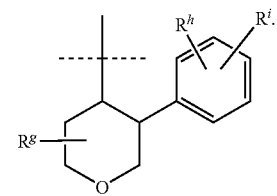

Within this embodiment (c), yet another group of compounds is that wherein A is a ring of formula:

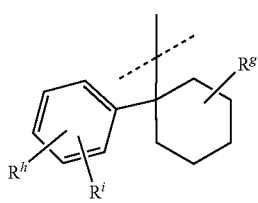

(d) Within the embodiments (III), A, B, (i)-(iii), (a), and (b) and groups contained therein, and groups formed as a result of combination of groups A, B, (i)-(iii), (a), (b), and groups contained therein, one group of compounds is that wherein $R^5$ is a ring of formula (ii).

Within this embodiment (d), yet another group of compounds is that wherein A is a ring of formula:

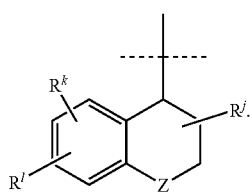

Within this group, one group of compounds is that wherein Z is —$CH_2$—. Within this group, one group of compounds is that wherein Z is —NH—. Within this group, one group of compounds is that wherein Z is —O—.

Within this embodiment (d), yet another group of compounds is that wherein A is a ring of formula:

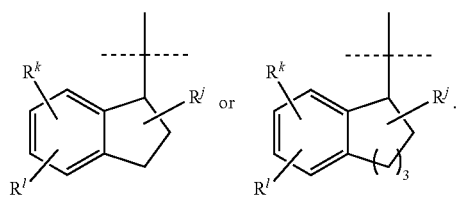

(e) Within the embodiments (III), A, B, (i)-(iii), (a), and (b) and groups contained therein, and groups formed as a result of combination of groups A, B, (i)-(iii), (a), (b), and groups contained therein, one group of compounds is that wherein $R^5$ is a ring of formula (iii).

Within this embodiment (e), yet another group of compounds is that wherein A is a ring of formula:

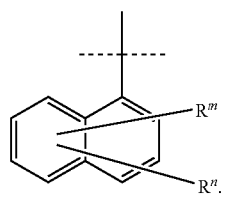

Within this embodiment (e), yet another group of compounds is that wherein A is a ring of formula:

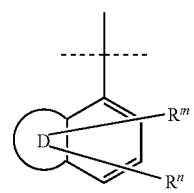

where D is a 5 or 6 membered heteroaryl ring.

Within the above groups (a)-(e), one group of compounds is that wherein $R^g$, $R^j$ and $R^m$ are independently hydrogen, alkyl, halo, haloalkyl, or haloalkoxy, preferably methyl, fluoro, chloro, trifluoromethyl, trifluoromethoxy or 2,2,2-trifluoroethoxy.

Within the above groups (a)-(e), yet another group of compounds is that wherein $R^g$, $R^j$ and $R^m$ are alkyl, halo, haloalkyl, or haloalkoxy, preferably methyl, fluoro, chloro, trifluoromethyl, trifluoromethoxy or 2,2,2-trifluoroethoxy, $R^h$, $R^k$ and $R^n$ are independently hydrogen, alkyl, halo, haloalkyl, or haloalkoxy, preferably hydrogen, methyl, fluoro, chloro, trifluoromethyl, trifluoromethoxy or 2,2,2-trifluoroethoxy and $R^i$ and $R^l$ are hydrogen.

(IV). Within embodiment (IA), in another embodiment the compound of Formula (I) is represented by the formula:

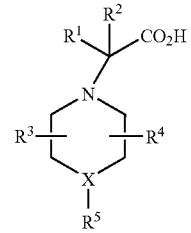

and $R^5$ is a ring of formula (iv)-(ix).
Within group (IV):
(A) In one embodiment, X is —CH—.
(B) In another embodiment, X is —N—.
(i) Within embodiments (IV), A and B, in one group of compounds, $R^1$ and $R^2$ are hydrogen.
(ii) Within embodiments (IV), A and B, in another group of compounds, $R^1$ is hydrogen and $R^2$ is alkyl.
(iii) Within embodiments (IV), A and B, in yet another group of compounds, $R^1$ is hydrogen and $R^2$ is methyl.
(a) Within embodiments (IV), A, B, (i)-(iii), and groups formed by combination of A, B and (i)-(iii), in one group of compounds, $R^3$ and $R^4$ are hydrogen.
(b) Within embodiments (IV), A, B, (i)-(iii), and groups formed by combination of A, B and (i)-(iii), another group of compounds is that wherein $R^3$ is hydrogen and $R^4$ is methyl, ethyl, or propyl and is located at the carbon atom that is ortho to the ring nitrogen atom substituted with —$CR^1R^2CO_2H$ group. Within this embodiment, one group of compounds is that wherein $R^4$ is methyl. Within this embodiment, one group of compounds is that wherein $R^4$ is methyl and the stereochemistry at the carbon atom carrying the $R^4$ group is (R). Within this embodiment, one group of compounds is that wherein $R^4$ is methyl and the stereochemistry at the carbon atom carrying the $R^4$ group is (S).
(c) Within the embodiments (IV), A, B, (i)-(iii), (a), and (b) and groups contained therein, and groups formed as a result of combination of groups A, B, (i)-(iii), (a), (b), and groups contained therein, one group of compounds is that wherein $R^5$ is a ring of formula (iv)

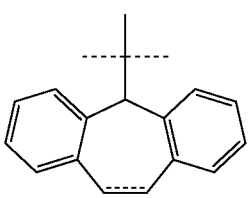

substituted with $R^r$, $R^s$, and $R^t$ as defined in the Summary. Within this group, one group of compounds is that wherein (iv) is has the structure:

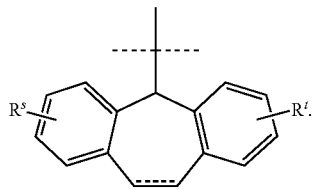

(d) Within the embodiments (IV), A, B, (i)-(iii), (a), and (b) and groups contained therein, and groups formed as a result of combination of groups A, B, (i)-(iii), (a), (b), and groups contained therein, one group of compounds is that wherein $R^5$ is a ring of formula (v)

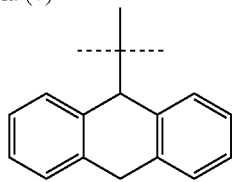

substituted with $R^r$, $R^s$, and $R^t$ as defined in the Summary.

Within this group, one group of compounds is that wherein $R^5$ has the structure:

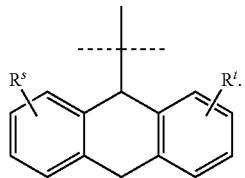

(e) Within the embodiments (IV), A, B, (i)-(iii), (a), and (b) and groups contained therein, and groups formed as a result of combination of groups A, B, (i)-(iii), (a), (b), and groups contained therein, one group of compounds is that wherein $R^5$ is a ring of formula (vi) substituted with $R^r$, $R^s$, and $R^t$ as defined in the Summary.

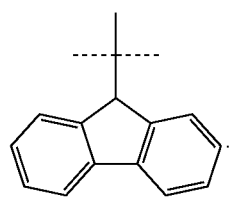

Within this group, one group of compounds is that wherein $R^5$ has the structure:

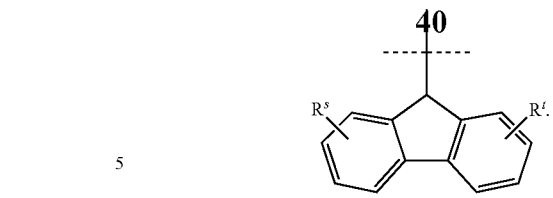

(f) Within the embodiments (IV), A, B, (i)-(iii), (a), and (b) and groups contained therein, and groups formed as a result of combination of groups A, B, (i)-(iii), (a), (b), and groups contained therein, one group of compounds is that wherein $R^5$ is a ring of formula (vii)

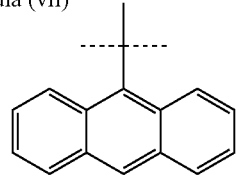

substituted with $R^r$, $R^s$, and $R^t$ as defined in the Summary. Within this group, one group of compounds is that wherein $R^5$ has the structure:

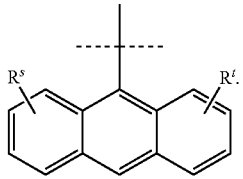

(g) Within the embodiments (IV), A, B, (i)-(iii), (a), and (b) and groups contained therein, and groups formed as a result of combination of groups A, B, (i)-(iii), (a), (b), and groups contained therein, one group of compounds is that wherein $R^5$ is a ring of formula (ix)

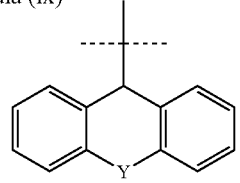

substituted with $R^r$, $R^s$, and $R^t$ as defined in the Summary. Within this group, one group of compounds is that wherein $R^5$ has the structure:

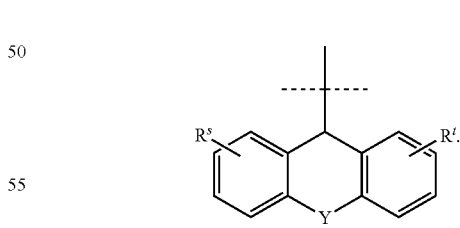

Within this group, one group of compounds is that wherein Y is —$CH_2$—. Within this group, one group of compounds is that wherein Y is —NH—. Within this group, one group of compounds is that wherein Y is —O—.

(h) Within the embodiments (IV), A, B, (i)-(iii), (a), and (b) and groups contained therein, and groups formed as a result of combination of groups I, II, (i)-(iii), (a), (b), and groups contained therein, one group of compounds is that wherein $R^5$ is a ring of formula (vi)

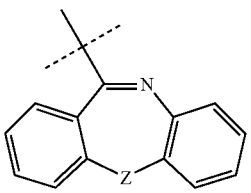

substituted with $R^r$, $R^s$, and $R^t$ as defined in the Summary. Within this group, one group of compounds is that wherein $R^5$ has the structure:

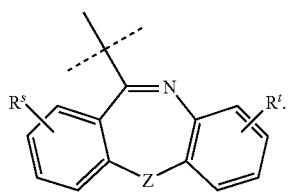

Within this group, one group of compounds is that wherein Z is —CH$_2$—. Within this group, one group of compounds is that wherein Z is —NH—. Within this group, one group of compounds is that wherein Z is —O—.

Within the above groups (a)-(h), one group of compounds is that wherein $R^s$ is alkyl, halo, haloalkyl, or haloalkoxy, preferably methyl, fluoro, chloro, trifluoromethyl, trifluoromethoxy or 2,2,2-trifluoroethoxy.

Within the above groups (a)-(h), one group of compounds is that wherein $R^s$ is alkyl, halo, haloalkyl, or haloalkoxy, preferably methyl, fluoro, chloro, trifluoromethyl, trifluoromethoxy or 2,2,2-trifluoroethoxy and $R^t$ is hydrogen, alkyl, halo, haloalkyl, or haloalkoxy, preferably hydrogen, methyl, fluoro, chloro, trifluoromethyl, trifluoromethoxy or 2,2,2-trifluoroethoxy.

(V). In yet another embodiment the compound of Formula (I) is represented by the formula:

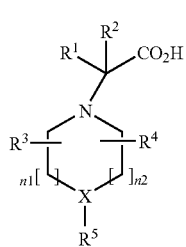

(I)

wherein:
X is —CH—;
$R^1$ and $R^2$ are independently hydrogen or alkyl;
$R^3$ and $R^4$ are independently hydrogen, alkyl, haloalkyl, alkoxy, or haloalkoxy;
n1 is 0 and n2 is 1 or 2; and
$R^5$ is as defined in the Summary.
In embodiment (V):
(A) In one embodiment, n1 is 0 and n2 are 1.
(B) In another embodiment n1 is 0 and n2 is 2.
(i) Within embodiments (V), A and B, in one group of compounds, $R^1$ and $R^2$ are hydrogen.
(ii) Within embodiments (V), A and B, in another group of compounds, $R^1$ is hydrogen and $R^2$ is alkyl.
(iii) Within embodiments (V), A and B, in yet another group of compounds, $R^1$ is hydrogen and $R^2$ is methyl.
(a) Within embodiments (V), A, B, (i)-(iii), and groups formed by combination of A, B and (i)-(iii), in one group of compounds, $R^3$ and $R^4$ are hydrogen.
(b) Within embodiments (V), A, B, (i)-(iii), and groups formed by combination of A, B and (i)-(iii), another group of compounds is that wherein $R^3$ is hydrogen and $R^4$ is methyl, ethyl, or propyl and is located at the carbon atom that is ortho to the ring nitrogen atom substituted with —CR$^1$R$^2$CO$_2$H group. Within this embodiment, one group of compounds is that wherein $R^4$ is methyl. Within this embodiment, one group of compounds is that wherein $R^4$ is methyl and the stereochemistry at the carbon atom carrying the $R^4$ group is (R). Within this embodiment, one group of compounds is that wherein $R^4$ is methyl and the stereochemistry at the carbon atom carrying the $R^4$ group is (S).
(c) Within the embodiments (V), A, B, (i)-(iii), (a), and (b) and groups contained therein, and groups formed as a result of combination of groups A, B, (i)-(iii), (a), (b), and groups contained therein, one group of compounds is that wherein $R^5$ is —CHAr$^1$Ar$^2$ or —NAr$^1$Ar$^2$ where Ar$^1$ and Ar$^2$ are independently aryl, heteroaryl, cycloalkyl, or heterocyclyl where each of the aforementioned ring is optionally substituted with $R^a$, $R^b$ or $R^c$ where $R^a$ is alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino and $R^b$ and $R^c$ are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, acylamino, aryl, heteroaryl, cycloalkyl, or heterocyclyl where the aromatic or alicyclic ring in $R^a$, $R^b$ and $R^c$ is optionally substituted with $R^d$, $R^e$ or $R^f$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino.

Within this embodiment (c), in one group of compounds $R^5$ is —CHAr$^1$Ar$^2$ where Ar$^1$ and Ar$^2$ are as defined above. Within this embodiment (c), in another group of compounds $R^5$ is —NAr$^1$Ar$^2$ where Ar$^1$ and Ar$^2$ are as defined above.

(i) Within embodiment (c) and embodiments contained therein, in one group of compounds is that wherein Ar$^1$ and Ar$^2$ are phenyl, each phenyl optionally substituted as defined therein.

Within group (i), one group of compounds is that wherein Ar$^1$ and Ar$^2$ are phenyl.

Within this embodiment (i), another group of compounds is that wherein Ar$^1$ is phenyl and Ar$^2$ is phenyl substituted with $R^a$ is alkyl, halo, haloalkyl, or haloalkoxy, preferably methyl, fluoro, chloro, trifluoromethyl, trifluoromethoxy or 2,2,2-trifluoroethoxy.

Within group (i), another group of compounds is that wherein Ar$^1$ is phenyl and Ar$^2$ is phenyl substituted with $R^a$ is alkyl, halo, haloalkyl, or haloalkoxy, preferably methyl, fluoro, chloro, trifluoromethyl, trifluoromethoxy or 2,2,2-trifluoroethoxy and $R^a$ is located at the 2-, 3-, or 4-, preferably 3-position of the phenyl ring, the carbon atom attached to the —CHAr$^1$ group being the 1-position.

Within group (i), another group of compounds is that wherein Ar$^1$ is phenyl substituted with $R^a$ selected from alkyl, halo, haloalkyl, or haloalkoxy, preferably methyl, fluoro, chloro, trifluoromethyl, trifluoromethoxy or 2,2,2-trifluoroethoxy, preferably $R^a$ is located at the 2-, 3-, or 4-, preferably 3-position of the phenyl ring and $Ar^2$ is phenyl substituted with $R^b$ selected from alkyl, halo, haloalkyl, or haloalkoxy, preferably methyl, fluoro, chloro, trifluoromethyl, preferably $R^b$ is located at the 2-, 3-, or 4-, preferably 3-position of the phenyl ring.

Within group (i), another group of compounds is that wherein $Ar^1$ and $Ar^2$ are phenyl independently optionally substituted with $R^b$ or $R^c$ where $R^b$ and $R^c$ are independently alkyl, halo, haloalkyl, haloalkoxy, cyano, or five or six membered heterocycle or heteroaryl provided that at least one of the phenyl is substituted i.e., covers compounds where one of the phenyl ring is mono or disubstituted and the other is unsubstituted or both rings are monosubstituted.

Within group (i), another group of compounds is that wherein $Ar^1$ is phenyl and $Ar^2$ is phenyl substituted with $R^a$ selected from alkyl, halo, haloalkyl, haloalkoxy or phenyl, preferably methyl, fluoro, chloro, trifluoromethyl, trifluoromethoxy, phenyl, or 2,2,2-trifluoroethoxy and $R^a$ is located at the 2-, 3-, or 4-, preferably 3-position of the phenyl ring, the carbon atom attached to the —$NAr^1$ group being the 1-position.

(ii) Within embodiment (c) and embodiments contained therein, another group of compounds is that wherein $Ar^1$ is phenyl and $Ar^2$ is heteroaryl, each optionally substituted as defined in the Summary.

Within group (ii), one group of compounds is that wherein $Ar^1$ is phenyl and $Ar^2$ is heteroaryl, preferably pyridinyl, pyrimidinyl, pyridazinyl, pyrazinyl, or thienyl, each $Ar^1$ and $Ar^2$ optionally substituted as defined in the Summary. Preferably, $Ar^1$ and $Ar^2$ are independently optionally substituted with $R^b$ or $R^c$ where $R^b$ and $R^c$ are independently alkyl, halo, haloalkyl, haloalkoxy, cyano, or five or six membered heterocycle or heteroaryl provided that at least one of $Ar^1$ and $Ar^2$ is substituted i.e., covers compounds where one of the phenyl or heteroaryl ring is mono or disubstituted and the other is unsubstituted or both rings are monosubstituted.

Within group (ii), another group of compounds is that wherein $Ar^1$ is phenyl and $Ar^2$ is pyridinyl, pyrimidinyl, pyridazinyl, pyrazinyl, or thienyl optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy.

Within group (ii), another group of compounds is that wherein $Ar^1$ is phenyl optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy and $Ar^2$ is pyridinyl, pyrimidinyl, pyridazinyl, pyrazinyl, or thienyl, preferably thienyl.

(iii) Within embodiment (c) and embodiments contained therein, yet another group of compounds is that wherein $Ar^1$ and $Ar^2$ are heteroaryl optionally substituted as defined in the Summary.

Within group (iii), one group of compounds is that wherein $Ar^1$ and $Ar^2$ are heteroaryl each optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy.

(iv) Within embodiment (c) and embodiments contained therein, yet another group of compounds is that wherein $Ar^1$ is phenyl and $Ar^2$ is heterocyclyl, each $Ar^1$ and $Ar^2$ optionally substituted as defined above.

Within this embodiment (iv), one group of compounds is that wherein $Ar^1$ is phenyl and $Ar^2$ is tetrahydropyranyl, piperidinyl, or tetrahydrofuranyl, each $Ar^1$ and $Ar^2$ optionally substituted as defined above.

Within this embodiment (iv), one group of compounds is that wherein $Ar^1$ is phenyl and $Ar^2$ is heterocyclyl, preferably tetrahydropyranyl, piperidinyl, or tetrahydrofuranyl optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy. Within this group, another group of compounds is that wherein $Ar^1$ is phenyl optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy and $Ar^2$ is tetrahydropyranyl, piperidinyl, or tetrahydrofuranyl.

(v) Within embodiment (c) and embodiments contained therein, yet another group of compounds is that wherein $Ar^1$ is phenyl and $Ar^2$ is cycloalkyl, each $Ar^1$ and $Ar^2$ optionally substituted as defined above.

Within this embodiment (v), one group of compounds is that wherein $Ar^1$ is phenyl and $Ar^2$ is cyclobutyl, cyclopentyl or cyclohexyl, each $Ar^1$ and $Ar^2$ optionally substituted as defined above.

Within this embodiment (v), one group of compounds is that wherein $Ar^1$ is phenyl and $Ar^2$ is cycloalkyl, preferably cyclobutyl, cyclopentyl or cyclohexyl, each $Ar^1$ and $Ar^2$ optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy.

Within this embodiment (v), one group of compounds is that wherein $Ar^1$ is phenyl and $Ar^2$ is cyclopropyl, $Ar^1$ optionally substituted as defined above.

Within this embodiment (v), one group of compounds is that wherein $Ar^1$ is phenyl and $Ar^2$ is cyclopropyl, $Ar^1$ optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy.

(vi) Within embodiment (c) and embodiments contained therein, yet another group of compounds is that wherein $Ar^1$ and $Ar^2$ are heteroaryl optionally substituted as defined above.

Within this embodiment (vi), one group of compounds is that wherein $Ar^1$ and $Ar^2$ are heteroaryl each optionally substituted with $R^a$ or $R^b$ independently selected from alkyl, halo, haloalkyl, or haloalkoxy, preferably methyl, fluoro, chloro, trifluoromethyl, trifluoromethoxy or 2,2,2-trifluoroethoxy.

(vii) Within embodiment (c) and embodiments contained therein, yet another group of compounds is that wherein $Ar^1$ is heteroaryl and $Ar^2$ is cycloalkyl each $Ar^1$ and $Ar^2$ optionally substituted as defined above.

(viii) Within embodiment (c) and embodiments contained therein, yet another group of compounds is that wherein $Ar^1$ is heterocyclyl and $Ar^2$ is heteroaryl each $Ar^1$ and $Ar^2$ optionally substituted as defined above.

(ix) Within embodiment (c) and embodiments contained therein, yet another group of compounds is that wherein $Ar^1$ is cycloalkyl and $Ar^2$ is heterocyclyl each $Ar^1$ and $Ar^2$ optionally substituted as defined above.

(x) Within embodiment (c) and embodiments contained therein, yet another group of compounds is that wherein $Ar^1$ is cycloalkyl and $Ar^2$ is cycloalkyl each $Ar^1$ and $Ar^2$ optionally substituted as defined above.

(d). Within the embodiments (V), A, B, (i)-(iii), (a), and (b) and groups contained therein, and groups formed as a result of combination of groups A, B, (i)-(iii), (a), (b), and groups contained therein, one group of compounds is that wherein $R^5$ is a ring of formula (i).

Within this embodiment (d), one group of compounds is that wherein $R^5$ is a ring of formula:

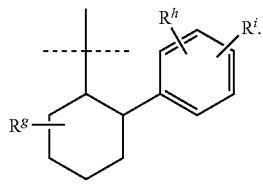

Within this embodiment (d), one group of compounds is that wherein $R^5$ is a ring of formula:

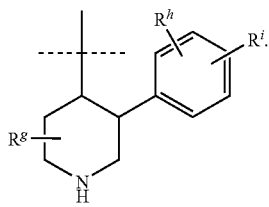

Within this embodiment (d), another group of compounds is that wherein A is a ring of formula:

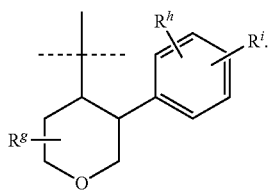

Within this embodiment (d), yet another group of compounds is that wherein A is a ring of formula:

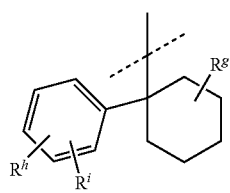

(e) Within the embodiments (V), A, B, (i)-(iii), (a), and (b) and groups contained therein, and groups formed as a result of combination of groups A, B, (i)-(iii), (a), (b), and groups contained therein, one group of compounds is that wherein $R^5$ is a ring of formula (ii).

Within this embodiment (e), yet another group of compounds is that wherein A is a ring of formula:

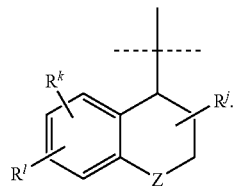

Within this group, one group of compounds is that wherein Z is —CH$_2$—. Within this group, one group of compounds is that wherein Z is —NH—. Within this group, one group of compounds is that wherein Z is —O—.

Within this embodiment (e), yet another group of compounds is that wherein A is a ring of formula:

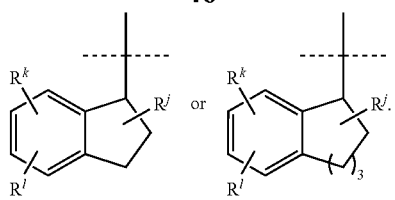

(f) Within the embodiments (V), A, B, (i)-(iii), (a), and (b) and groups contained therein, and groups formed as a result of combination of groups A, B, (i)-(iii), (a), (b), and groups contained therein, one group of compounds is that wherein $R^5$ is a ring of formula (iii).

Within this embodiment (f), yet another group of compounds is that wherein A is a ring of formula:

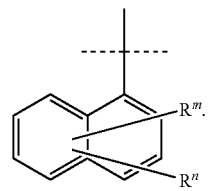

Within this embodiment (f), yet another group of compounds is that wherein A is a ring of formula:

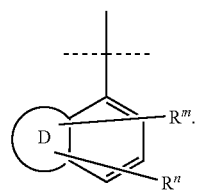

where D is a 5 or 6 membered heteroaryl ring.

Within the above groups (d)-(f), one group of compounds is that wherein $R^g$, $R^j$ and $R^m$ are independently hydrogen, alkyl, halo, haloalkyl, or haloalkoxy, preferably methyl, fluoro, chloro, trifluoromethyl, trifluoromethoxy or 2,2,2-trifluoroethoxy.

Within the above groups (d)-(f), yet another group of compounds is that wherein $R^g$, $R^j$ and $R^m$ are alkyl, halo, haloalkyl, or haloalkoxy, preferably methyl, fluoro, chloro, trifluoromethyl, trifluoromethoxy or 2,2,2-trifluoroethoxy, $R^h$, $R^k$ and $R^n$ are independently hydrogen, alkyl, halo, haloalkyl, or haloalkoxy, preferably hydrogen, methyl, fluoro, chloro, trifluoromethyl, trifluoromethoxy or 2,2,2-trifluoroethoxy and $R^i$ and $R^l$ are hydrogen.

(g) Within the embodiments (V), A, B, (i)-(iii), (a), and (b) and groups contained therein, and groups formed as a result of combination of groups A, B, (i)-(iii), (a), (b), and groups contained therein, one group of compounds is that wherein $R^5$ is a ring of formula (iv)

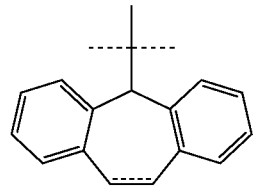

substituted with $R^r$, $R^s$, and $R^t$ as defined in the Summary. Within this group, one group of compounds is that wherein (iv) is has the structure:

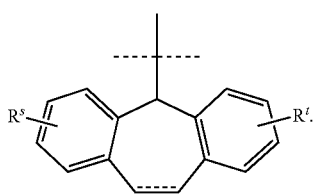

(h) Within the embodiments (V), A, B, (i)-(iii), (a), and (b) and groups contained therein, and groups formed as a result of combination of groups A, B, (i)-(iii), (a), (b), and groups contained therein, one group of compounds is that wherein $R^5$ is a ring of formula (v)

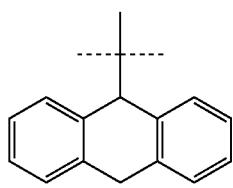

substituted with $R^r$, $R^s$, and $R^t$ as defined in the Summary.
Within this group, one group of compounds is that wherein $R^5$ has the structure:

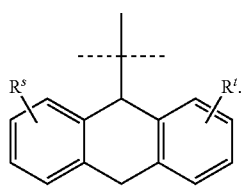

(i) Within the embodiments (V), A, B, (i)-(iii), (a), and (b) and groups contained therein, and groups formed as a result of combination of groups A, B, (i)-(iii), (a), (b), and groups contained therein, one group of compounds is that wherein $R^5$ is a ring of formula (vi) substituted with $R^r$, $R^s$, and $R^t$ as defined in the Summary.

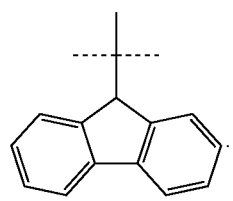

Within this group, one group of compounds is that wherein $R^5$ has the structure:

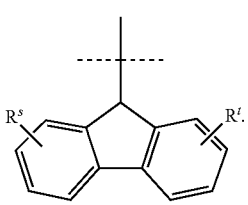

(j) Within the embodiments (V), A, B, (i)-(iii), (a), and (b) and groups contained therein, and groups formed as a result of combination of groups A, B, (i)-(iii), (a), (b), and groups contained therein, one group of compounds is that wherein $R^5$ is a ring of formula (vii)

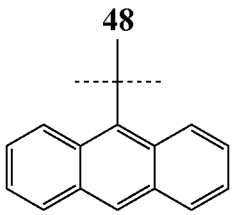

substituted with $R^r$, $R^s$, and $R^t$ as defined in the Summary.
Within this group, one group of compounds is that wherein $R^5$ has the structure:

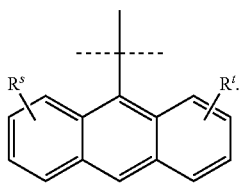

(k) Within the embodiments (V), A, B, (i)-(iii), (a), and (b) and groups contained therein, and groups formed as a result of combination of groups A, B, (i)-(iii), (a), (b), and groups contained therein, one group of compounds is that wherein $R^5$ is a ring of formula (ix)

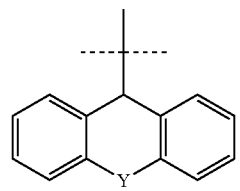

substituted with $R^r$, $R^s$, and $R^t$ as defined in the Summary.
Within this group, one group of compounds is that wherein $R^5$ has the structure:

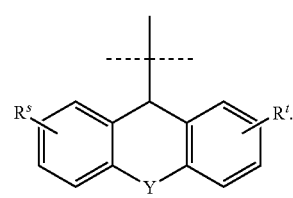

Within this group, one group of compounds is that wherein Y is —$CH_2$—. Within this group, one group of compounds is that wherein Y is —NH—. Within this group, one group of compounds is that wherein Y is —O—.

(l) Within the embodiments (V), A, B, (i)-(iii), (a), and (b) and groups contained therein, and groups formed as a result of combination of groups A, B, (i)-(iii), (a), (b), and groups contained therein, one group of compounds is that wherein $R^5$ is a ring of formula (vi)

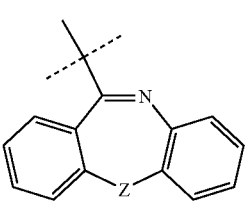

substituted with R$^r$, R$^s$, and R$^t$ as defined in the Summary. Within this group, one group of compounds is that wherein R$^5$ has the structure:

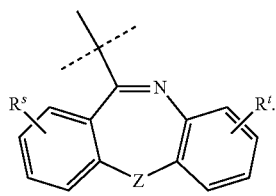

Within this group, one group of compounds is that wherein Z is —CH$_2$—. Within this group, one group of compounds is that wherein Z is —NH—. Within this group, one group of compounds is that wherein Z is —O—.

Within the above groups (g)-(l), one group of compounds is that wherein R$^b$ is alkyl, halo, haloalkyl, or haloalkoxy, preferably methyl, fluoro, chloro, trifluoromethyl, trifluoromethoxy or 2,2,2-trifluoroethoxy.

Within the above groups (g)-(l), one group of compounds is that wherein R$^b$ is alkyl, halo, haloalkyl, or haloalkoxy, preferably methyl, fluoro, chloro, trifluoromethyl, trifluoromethoxy or 2,2,2-trifluoroethoxy and R$^t$ is hydrogen, alkyl, halo, haloalkyl, or haloalkoxy, preferably hydrogen, methyl, fluoro, chloro, trifluoromethyl, trifluoromethoxy or 2,2,2-trifluoroethoxy.

(VI). In yet another embodiment the compounds of Formula (I) are those wherein R$^5$ is —NAr$^1$Ar$^2$ where Ar$^1$ and Ar$^2$ are as defined in the Summary of the Invention.

(VII). In yet another embodiment the compounds of Formula (I) are those wherein R$^5$ is —CHAr$^1$Ar$^2$ where Ar$^1$ and Ar$^2$ are as defined in the Summary of the Invention.

Within embodiments (VI) and (VII), in one group of compounds Ar$^1$ is phenyl and Ar$^2$ is heteroaryl, preferably pyridinyl, pyrimidinyl, pyridazinyl, pyrazinyl, or thienyl, each Ar$^1$ and Ar$^2$ optionally substituted as defined in the Summary. Preferably, Ar$^1$ and Ar$^2$ are each independently substituted with R$^b$ and/or R$^c$ where R$^b$ and R$^c$ are independently alkyl, halo, haloalkyl, haloalkoxy, cyano, or five or six membered heterocycle or heteroaryl i.e., covers compounds where one of the phenyl and heteroaryl ring is disubstituted and the other is unsubstituted or both rings are monosubstituted or only one ring is monosubstituted.

Within embodiments (VI) and (VII), in another group of compounds Ar$^1$ and Ar$^2$ are phenyl, each Ar$^1$ and Ar$^2$ optionally substituted as defined in the Summary. Preferably, Ar$^1$ and Ar$^2$ are each independently substituted with R$^b$ and/or R$^c$ where R$^b$ and R$^c$ are independently alkyl, halo, haloalkyl, haloalkoxy, cyano, or five or six membered heterocycle or heteroaryl i.e., covers compounds where one of the phenyl ring is disubstituted and the other is unsubstituted or both rings are monosubstituted or only one ring is monosubstituted. Preferably, Ar$^1$ is phenyl and Ar$^2$ is phenyl substituted with R$^a$ where R$^a$ is alkyl, halo, haloalkyl, haloalkoxy, or phenyl, preferably methyl, chloro, fluoro, trifluoromethyl, trifluoromethoxy or phenyl, preferably R$^a$ is located at the carbon meta to the one attached to —CH—Ar$^1$ or —NAr$^1$ group.

Within embodiments (VI) and (VII), in another group of compounds Ar$^1$ and Ar$^2$ are each independently substituted with R$^b$ and/or R$^c$ where R$^b$ and R$^c$ are independently alkyl, halo, haloalkyl, haloalkoxy, cyano, or five or six membered heterocycle or heteroaryl, preferably methyl, chloro, bromo, fluoro, trifluoromethyl, trifluoromethoxy, cyano, thienyl, pyridinyl, or pyrrolidin-1-yl i.e., covers compounds where one of the phenyl and heteroaryl ring is disubstituted and the other is unsubstituted or both rings are monosubstituted or only one ring is monosubstituted. Preferably Ar$^1$ is selected from phenyl, cyclopropyl, cyclopentyl, cyclohexyl, thienyl, pyrrolyl, pyridyl, tetrahydrofuranyl, or pyridiminyl and Ar$^2$ is phenyl independently substituted as described above.

Within embodiments (VI) and (VII), and groups contained therein, in one group of compounds R$^1$ and R$^2$ are hydrogen.

Within embodiments (VI) and (VII), and groups contained therein, in one group of compounds R$^3$ and R$^4$ are hydrogen. Preferably, R$^3$ and R$^4$ are hydrogen when n1 is 0 and n2 is 1.

Within embodiments (VI) and (VII), and groups contained therein, in another group of compounds R$^3$ is hydrogen and R$^4$ is alkyl, preferably R$^4$ is methyl and is located at the carbon atom ortho to the nitrogen substituted with the —CR$^1$R$^2$CO$_2$H, preferably when n1 and n2 are 1.

(VIII). In yet another embodiment the compounds of Formula (I) are those wherein R$^5$ is a ring of formula (i), (ii), or (iii).

(IX). In yet another embodiment the compounds of Formula (I) are those wherein R$^5$ is a ring of formula (iv)-(ix).

Within embodiments (VIII) and (IX), in one group of compounds R$^1$ and R$^2$ are hydrogen.

Within embodiments (VIII) and (IX), and groups contained therein, in one group of compounds R$^3$ and R$^4$ are hydrogen. Preferably, R$^3$ and R$^4$ are hydrogen when n1 is 0 and n2 is 1.

Within embodiments (VIII) and (IX), and groups contained therein, in another group of compounds R$^3$ is hydrogen and R$^4$ is alkyl, preferably R$^4$ is methyl and is located at the carbon atom ortho to the nitrogen substituted with the —CR$^1$R$^2$CO$_2$H, preferably when n1 and n2 are 1.

(X). In yet another embodiment the compounds of Formula (I) are those where R$^3$ and R$^4$ are hydrogen. Preferably, R$^3$ and R$^4$ are hydrogen when n1 is 0 and n2 is 1.

(XI). In yet another embodiment the compounds of Formula (I) are those where R$^3$ is hydrogen and R$^4$ is alkyl, preferably R$^4$ is methyl and is located at the carbon atom ortho to the nitrogen substituted with the —CR$^1$R$^2$CO$_2$H, preferably when n1 and n2 are 1.

(XII). In yet another embodiment the compounds of Formula (I) are those where R$^1$ and R$^2$ are hydrogen. Within this embodiment (XII), in one group of compounds R$^3$ and R$^4$ are hydrogen. Within this embodiment (XII), in another group of compounds R$^3$ is hydrogen and R$^4$ is alkyl, preferably R$^4$ is methyl and is located at the carbon atom ortho to the nitrogen substituted with the —CR$^1$R$^2$CO$_2$H, preferably when n1 and n2 are 1.

(XIII). In yet another embodiment the compounds of Formula (I) are those where Ar$^1$ and Ar$^2$ are phenyl.

(XIV). In yet another embodiment the compounds of Formula (I) are those where wherein Ar$^1$ and Ar$^2$ are phenyl substituted with R$^a$, R$^b$ or R$^c$. Preferably, wherein Ar$^1$ and Ar$^2$ are each independently optionally substituted with R$^b$ or R$^c$ where R$^b$ and R$^c$ are independently alkyl, halo, haloalkyl, haloalkoxy, cyano, or five or six membered heterocycle or heteroaryl, preferably alkyl, halo, haloalkyl, haloalkoxy, or cyano; provided at least one of Ar$^1$ and Ar$^2$ is substituted i.e., covers compounds where one of Ar$^1$ and Ar$^2$ is mono- or disubstituted and the other is unsubstituted or both rings are monosubstituted.

(XV). In yet another embodiment the compounds of Formula (I) have the structure:

(a) 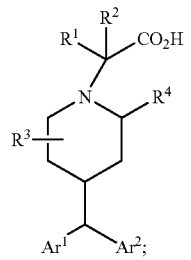

(b) 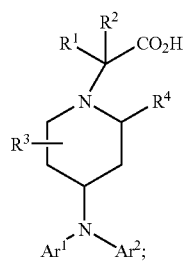

(c) 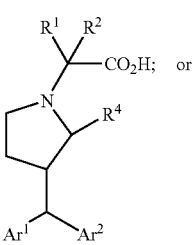 or (d) 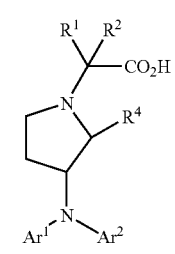

Preferably (b), (c) or (d); wherein $R^1$ and $R^2$ are independently H or alkyl, preferably H;

$R^3$ is hydrogen or alkyl, preferably hydrogen;

$R^4$ is hydrogen or alkyl, preferably hydrogen or methyl, more preferably in structure (a) and (b) $R^4$ is methyl and (c) and (b) $R^4$ is hydrogen; and $Ar^1$ and $Ar^2$ are phenyl each independently substituted with $R^a$ and/or $R^b$ independently selected from hydrogen, alkyl, halo, haloalkyl, or 5 or 6 membered heteroaryl. Preferably $Ar^1$ is is phenyl and $Ar^2$ is phenyl substituted with $R^a$ selected from alkyl, halo, haloalkyl, or 5 or 6 membered heteroaryl, more preferably methyl, trifluoromethyl, or pyridinyl, even more preferably $R^a$ is located at the 3-position of the phenyl ring, the carbon atom of the phenyl ring attached to —$CHAr^1$ or —$NAr^1$ being the 1-position.

The above embodiments, include all combinations of individual groups and subs-groups contained therein.

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of Formula (I) where X is —CH—, n1 and n2 are 1, and $R^5$ is —$NAr^1Ar^2$ where $Ar^1$, $Ar^2$, $R^1$, $R^2$, $R^3$, and $R^4$ are as defined in the Summary of the Invention can be prepared as illustrated and described in Scheme A below.

Scheme A

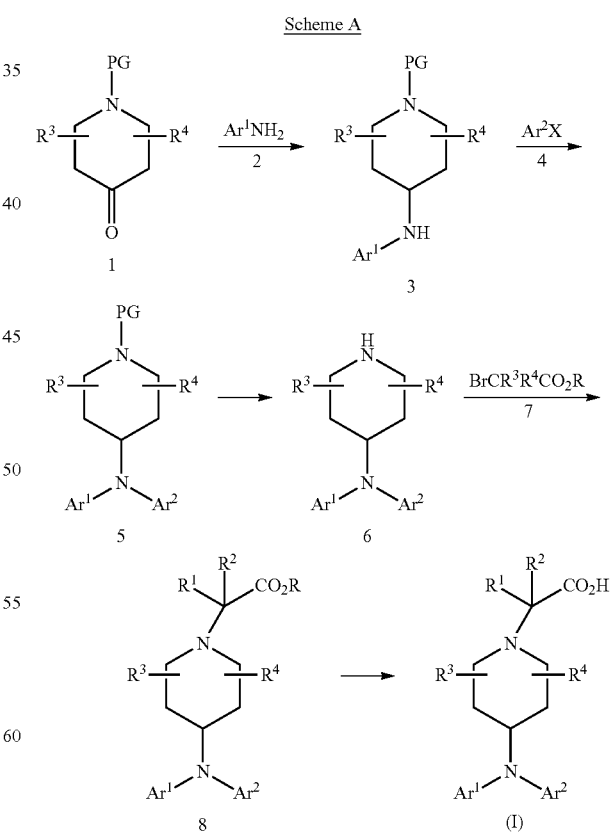

Treatment of a keto compound of formula 1 where PG is a suitable protecting group such as tert-butoxycarbonyl, benzyl, and the like, $R^3$ and $R^4$ are as defined in the Summary of the Invention, with an amino compound of formula 2 where $Ar^1$ as defined in the Summary of the Invention, under reductive amination conditions provides a compound of formula 3. The reaction is typically carried out in the presence of a suitable reducing agent (e.g., sodium cyanoborohydride, sodium triacetoxyborohydride, and the like) and an organic acid (e.g., glacial acetic acid, trifluoroacetic acid, and the like) at ambient temperature. Suitable solvents for the reaction are halogenated hydrocarbons (e.g., 1,2-dichloroethane, chloroform, and the like) or MeOH.

Compounds of formula 1 and 2 are either commercially available or can be readily prepared by methods well known in the art. For example, Boc-4-piperidone and aniline are commercially available. Compounds of formula 2 can also be prepared from corresponding nitro compounds by reduction of the nitro group under conditions well known in the art.

Compound 3 is then reacted with a compound of formula 4 where X is halo and $Ar^2$ is as defined in the Summary of the Invention under Buchwald reaction conditions to provide a compound of formula 5. Compounds of formula 4 are either commercially available or can be readily prepared by methods well known in the art.

Removal of the PG group in 5 provides a compound of formula 6. The reaction conditions for removal of the PG group depend on the nature of the protecting group. For example, if PG is tert-butoxycarbonyl, it is removed under acidic hydrolysis reaction conditions. If it is benzyl, then it is removed under catalytic hydrogenation reaction conditions.

Treatment of compound 6 with bromoacetate of formula 7 where R is alkyl, preferably methyl, ethyl, tert-butyl, and the like provides a compound of formula 8. The reaction is carried out in the presence of a base such as triethylamine, DIPEA, and the like and in a suitable organic solvent such as acetonitrile, tetrahydrofuran, DMF, methylene chloride, and the like. Acidic or basic hydrolysis of the ester group in 8 then provides the compound of Formula (I).

Compounds of formula 8 can be further modified prior to converting it to a compound of Formula (I). For example, a compound of formula 8 where $Ar^1$ or $Ar^2$ is substituted with a halo group, can be reacted with aryl, or heteroarylboronic acids under Suzuki coupling reaction conditions to provide a corresponding compound of formula 8 where $Ar^1$ or $Ar^2$ is substituted with aryl, or heteroaryl ring, respectively. The reaction is usually carried out in the presence of common palladium catalysts such as $Pd(PPh_3)_4$, $Pd(PPh_3)_2Cl_2$, $Pd_2dba_3$, $Pd(dppf)Cl_2 \cdot CH_2Cl_2$ and the like, and a weak base such as $Na_2CO_3$ and the like, in a mixture of solvents of water and a suitable organic solvent such as acetonitrile, p-dioxane, DMF, THF and the like. The reaction is usually heated up to 70-130° C. temperature range (oil bath or microwave irradiation). Acidic hydrolysis of the ester group in 8 then provides the compound of Formula (I).

Alternatively, the above transformation can be carried out under Stille coupling reaction conditions. Under Stille reaction conditions, the compound 8 where $Ar^1$ or $Ar^2$ is substituted with a halo group is treated with aryl, heteroaryltributyltin (or trimethyltin) derivatives to provide a compound of formula 8 where $Ar^1$ or $Ar^2$ is substituted with aryl, or heteroaryl ring, respectively. The reaction is usually carried out in the presence of common palladium catalysts such as $Pd(PPh_3)_4$, $Pd(PPh_3)_2Cl_2$, $Pd_2 dba_3$, $Pd(dppf)Cl_2 \cdot CH_2Cl_2$ and the like, and with or without additional ligands such as $tBu_3P$, $Ph_3P$, $Ph_3As$, and the like, in a suitable organic solvent such as toluene, acetonitrile, p-dioxane, DMF, THF and the like. The reaction temperature ranges from 20 to 150° C. (rt, oil bath or microwave irradiation). Acidic hydrolysis of the ester group in 8 then provides the compound of Formula (I).

Compounds of Formula 8 where $Ar^1$ or $Ar^2$ is substituted with mono substituted or disubstituted amino as defined in the Summary of the Invention can be prepared from a corresponding compound of Formula 8 where $Ar^1$ or $Ar^2$ is substituted with nitro group by first reducing the nitro group to an amino group and then alkylating, arylating, sulfonylating or acylating the amino group under conditions well known in the art. The mono substituted amino can be converted to the disubstituted amino, if desired, by alkylating, arylating, sulfonylating, or acylating the monosubstituted amino. The reaction is typically carried out in the presence of a base such as potassium tert-butoxide, and the like, and a catalyst such as 18-crown-6 in a suitable solvent such as tetrahydrofuran, and the like. Acidic hydrolysis of the ester group in 8 then provides the compound of Formula (I).

Compounds of Formula 8 where $Ar^1$ or $Ar^2$ is substituted with alkoxy, haloalkoxy, hydroxyalkoxy, or aminoalkoxy can be prepared by treating a corresponding compound of Formula 8 where $Ar^1$ or $Ar^2$ is substituted with hydroxy with alkyl halide, alkoxy halide, aminoalkyl halide or haloalkyl in the presence of a base. Acidic hydrolysis of the ester group in 8 then provides the compound of Formula (I).

Similarly, compounds of Formula (I) where X is —CH—, n1 is 0 and n2 are 1 or 2, and $R^5$ is —$NAr^1Ar^2$ where $Ar^1$, $Ar^2$, $R^1$, $R^2$, $R^3$, and $R^4$ are as defined in the Summary of the Invention can be prepared utilizing commercially available starting materials.

It will be recognized by a person skilled in the art that the above transformations could also be carried out at earlier stages in the synthetic process based on feasibility of the transformations.

Compounds of Formula (I) where X is —CH—, n1 0 or 1 and n2 are 1, and $R^5$ is —$CHAr^1Ar^2$ where $Ar^1$, $Ar^2$, $R^1$, $R^2$, $R^3$, and $R^4$ are as defined in the Summary of the Invention can be prepared as illustrated and described in Scheme B below.

Scheme B

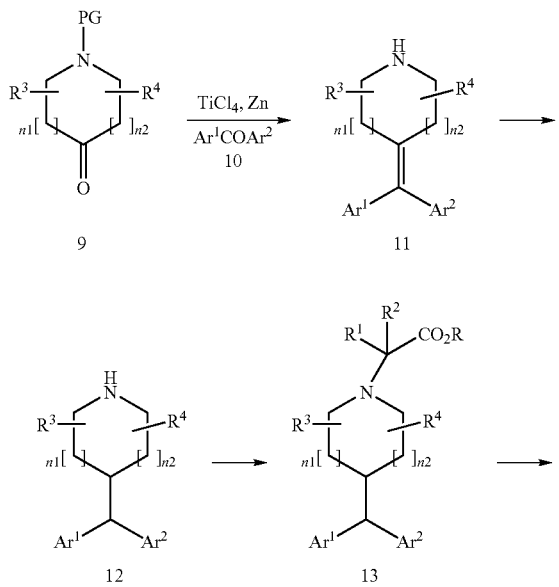

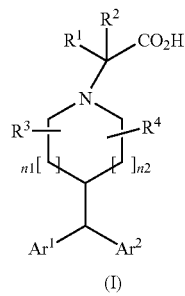

Treatment of a piperidone compound of formula 9 where PG is a suitable protecting group such as tert-butoxycarbonyl and the like, and $R^3$ and $R^4$ are as defined in the Summary of the Invention, with a keto compound of formula 10 where $Ar^1$ and $Ar^2$ are as defined in the Summary of the Invention, in the presence of titanium tetrachloride and zinc under McMurry coupling reaction conditions provides a compound of formula 11. The reaction is typically carried out in a suitable solvent such as tetrahydrofuran.

Compounds of formula 9 and 10 are either commercially available or can be readily prepared by methods well known in the art. For example, 1-Boc-4-oxopiperidine, 1-Boc-3-oxopiperidine and 1-Boc-3-oxopyrrolidine are commercially available. Compounds of formula $Ar^1COAr^2$ such as (2-bromophenyl)(phenyl)methanone, 4-bromobenzophenone, 2-fluorobenzophenone, 2,4-difluorobenzophenone, (4-fluorophenyl)-(phenyl)methanone, 2-(trifluoromethyl)-benzophenone, 3-(trifluoromethyl)-benzophenone, 4-(trifluoromethyl)-benzophenone, 3,4-dichlorobenzophenone, 4-chloro-benzophenone, 2-hydroxybenzophenone, 2,4-dihydroxybenzophenone, 3-hydroxybenzophenone, 5-chloro-2-hydroxy-4-methyl-benzophenone, 4-hydroxybenzophenone, 2-hydroxy-5-methyl-benzophenone, 3-benzoylbenzoic acid, 4-benzoylbenzoic acid, 4-benzoylbiphenyl, 4-amino-3-nitrobenzophenone, 3-nitro-benzophenone, 2-chloro-5-nitro-benzophenone, 4-nitro-benzophenone, 2-amino-5-nitro-benzophenone, 2-amino-benzophenone, 3,4-diaminobenzophenone, 2-amino-5-chloro-benzophenone, 4-aminobenzophenone, 4-(dimethylamino)-benzophenone, 2-hydroxy-4-methoxy-benzophenone, 4-methoxy-benzophenone, 2-methylbenzophenone, 3-methyl-benzophenone, (2,4-dimethyl-phenyl)(phenyl)methanone, 4-methylbenzophenone, 3-chloro-benzophenone, 3,4-difluorobenzophenone, 4-cyanobenzophenone, (3-aminophenyl)-(phenyl)methanone, 3,4-dihydroxybenzophenone, 4-fluorobenzophenone, 2-benzoylbenzoic acid, 2-benzoyl-naphthalene, 4-chloro-3-nitro-benzophenone, 3,4-dimethylbenzophenone, 2,5-difluoro-benzophenone, 1,4-dibenzoylbenzene, 4-ethylbenzophenone, 3,5-bis(trifluoromethyl)-benzophenone, 3-amino-benzophenone, 2-methoxybenzophenone, 1-naphthyl phenyl ketone, 2,3-difluoro-benzophenone, 3,5-difluorobenzophenone, 2-fluoro-5-(trifluoromethyl)-benzophenone, 4-fluoro-3-(trifluoromethyl)benzophenone, 4-benzoyl-4'-bromobiphenyl, 6-benzoyl-2-naphthol, 2-amino-4-methylbenzophenone, 5-chloro-2-(methylamino)-benzophenone, 2,5-dimethylbenzophenone, methyl 2-benzoylbenzoate, 4-benzyloxybenzophenone, 5-chloro-2-hydroxybenzophenone, 2-fluoro-3-(trifluoromethyl)-benzophenone, 4-(diethylamino)-benzophenone, 3-bromobenzophenone, 2-cyanobenzophenone, 4-ethoxy-2-hydroxybenzophenone, 2-chlorobenzophenone, are commercially available from Lancaster Synthesis Ltd.; Fluka Chemie GmbH; Aldrich Chemical Company, Inc.; Alfa Aesar, A Johnson Matthey Company; Acros Organics USA; Maybridge; or VWR International.

The double bond in compound 11 can be reduced under suitable reducing conditions such as Pd/C/ under $H_2$ to give a compound of formula 12. Compound 12 is then converted to a compound of Formula (I) as described in Scheme A above.

Alternatively, compounds of Formula (I) X is —CH—, n1 and n2 are 1, and $R^5$ is —CHAr$^1$Ar$^2$ where $Ar^1$, $Ar^2$, $R^1$, $R^2$, $R^3$, and $R^4$ are as defined in the Summary of the Invention can be prepared as illustrated and described in Scheme C below.

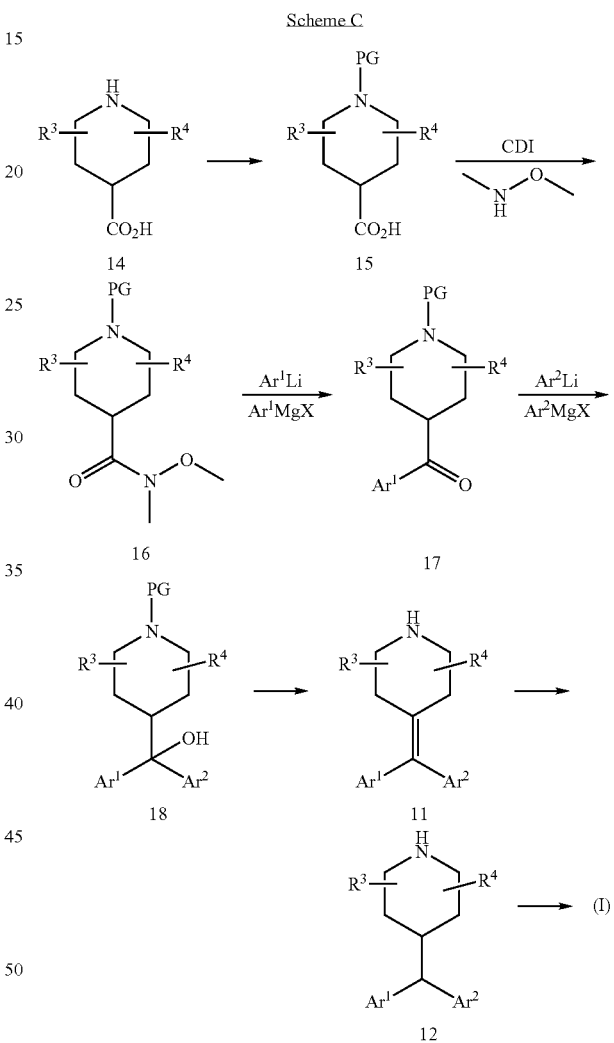

Protection of a 4-piperidinyl carboxylic acid of formula 14 with a suitable protecting group such as Boc or CBz provides the corresponding compound of formula 15. Coupling of compound 15 with N-methoxymethanamine in a suitable organic solvent such as dichloromethane, and the like, provides a Weinreb amide of formula 16. Compound 16 is treated with an organolithium compound of formula Ar$^1$Li or a Grignard reagent of formula Ar$^1$MgX where X is halo to give a keto compound of formula 17, which upon treatment with a second oganonlithium compound of formula Ar$^2$Li or a Grignard reagent of formula Ar$^2$MgX as described above provides a compound an alcohol of formula 18. Dehydration and removal of the protecting group in compound 18 with trifluoroacetic acid in one pot provides compound 11 which is then converted to a compound of Formula (I) as described in Scheme B above.

Compounds of Formula (I) where X is —N—, n1 and n2 are 1, $R^5$ is a ring of formula (i)-(ix) and $R^1$, $R^2$, $R^3$, $R^4$ and $R^5$ are as defined in the Summary of the Invention can be prepared as illustrated and described in Scheme D below.

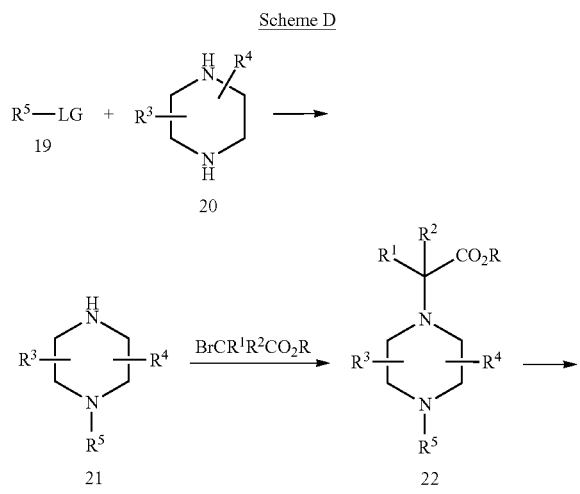

Scheme D

Treatment of a compound of formula 19 where LG is a suitable leaving group such as halo, tosylate, mesylate, triflate, and the like, and $R^5$ is a ring of formula (i)-(ix) as defined in the Summary of the Invention with a piperazine of formula 20 where $R^3$ and $R^4$ are as defined in the Summary of the Invention, provides a compound of formula 21. The reaction is carried out in a suitable organic solvent such as acetonitrile, toluene, and the like (with or without a base such as triethylamine or diisopropylethylamine) and takes place upon heating at a suitable temperature between 70 to 150° C.

Compounds of formula 19 are either commercially available or can be readily prepared by methods well known in the art. For example, compounds of formula 19 where LG is halo can be prepared by reduction of a corresponding ketone compound (i.e., where $R^5$ is a ring of formula (i), (ii), (iv), (v), (vi) or (viii) having a keto group in the ring) with a suitable reducing agent such as sodium borohydride, and the like, in a suitable organic alcohol solvent such as methanol, ethanol, and the like to provide the corresponding alcohol which upon treatment with a halogenating agent such as thionyl chloride, oxalyl chloride, triphenylphosphine/carbon tetrabromide, and the like provides the compound of formula 19 where LG is halo.

Alternatively, the alcohol can be treated with mesyl chloride, tosyl chloride, triflic anhydride under conditions well known in the art to provide a compound of formula 19 where LG is mesylate, tosylate, or triflate, respectively.

Alternatively, a compound of formula 21 can be prepared from the keto compound under reductive amination reaction conditions. The reaction is typically carried out in the presence of $NaH(OAc)_3$, with or without acetic acid. In some instances, the reaction may be carried out in the presence of $Ti(OiPr)_4$ at 20-80° C., followed by $NaBH_4$ reduction in methanol or ethanol.

Ketones such as 1-indanone, 5-methoxy-1-indanone, 5-bromo-1-indanone, 2-methyl-1-indanone, 6-bromo-1-indanone, alpha-tetralone, 2-methyl-1-tetralone, 6-methoxy-1-tetralone, 7-methoxy-1-tetralone, 7-bromo-3,4-dihydro-1 (2H)-naphthalenone, 6-bromo-tetral-1-one, 9-fluorenone, 2,7-dibromo-9-fluorenone, anthrone, xanthone, 3,6-dimethoxyxanthone, thioxanthen-9-one, 2-(trifluoromethyl) thioxanthen-9-one, dibenzosuberone, 2-methoxy-dibenzo-suberone, dibenzosuberenone, dibenzo[b,f]thiepin-10(11H)-one, dibenzo[b,f][1,4]thiazepine-11-[10H]one, 5,10-dihydro-dibenzo[b,e][1,4]diazepin-11-one, 8-chloro-5, and 10-dihydro-11H-dibenzo[b,e][1,4]-diazepin-11-one and 7-bromo-3,4-dihydro-1(2H)-naphthalenone are commercially available or they can also be prepared by methods well known in the art.

For example, ketones that can be used to prepared ring (i) where ring B is ortho to the carbon attached to the piperazine ring can be prepared as follows:

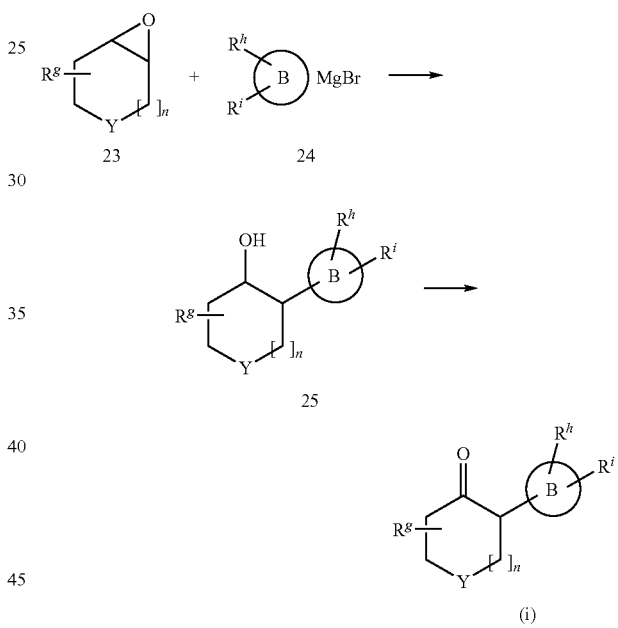

Treatment of an epoxide compound of formula 23 with a Grignard reagent 24 where ring B is as defined in the Summary of the Invention provides a compound of formula 25. The reaction is carried out in the presence of copper bromide and dimethylsulfide at 0° C. in an organic solvent such as tetrahydrofuran, and the like. Oxidation of the hydroxyl group in 25 with a suitable oxidizing reagent such as Dess Martin reagent or under Swern oxidation reaction conditions then provides a ring of formula (i). Epoxide of formula 23 can be prepared by the method described in *Tetrahedron*, 1974, 30, 4013.

Compound 21 is then converted to a compound of Formula (I) as described in Scheme A above.

Compounds of Formula (I) where $R^5$ is a ring of formula (i) where ring B is attached to carbon that is attached to the piperazine ring can be prepared as shown below.

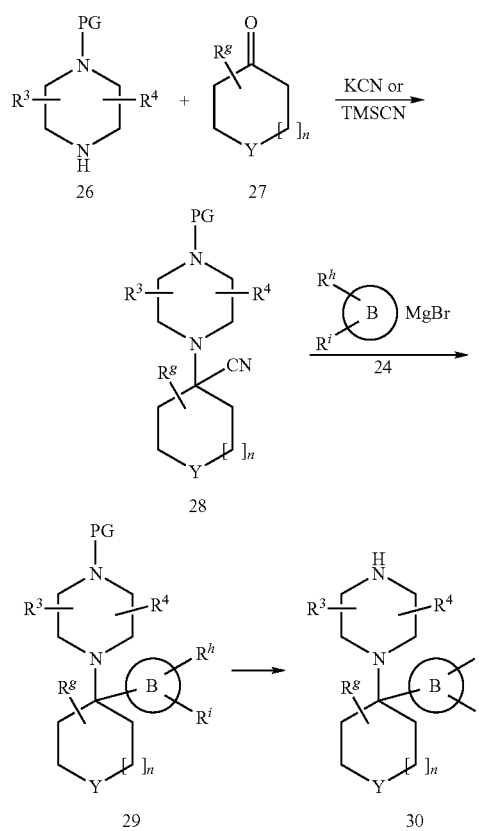

Treatment of a piperazine compound of formula 26 where $R^3$ and $R^4$ are as defined in the Summary of the Invention and PG is a suitable protecting group such as Boc, CBz, and the like with a keto compound of formula 27 in the presence of KCN or TMSCN under weakly acidic conditions provides a compound of formula 28. Compound 28 is then reacted with a Grignard reagent or organolithium reagent of formula 24 where ring B is as defined in the Summary of the Invention provides a compound of formula 29 which upon removal of the amino protecting group to give a compound of formula 30. Compound 30 is then converted to a compound of Formula (I) as described above.

Compounds of formula 26 and 27 are either commercially available or they can be prepared by methods well known in the art. For example, 1-Boc-piperazine, (2R,5S)-2,5-dimethyl-piperazine-1-carboxylic acid tert-butyl ester, (R)—N-1-Boc-2-(benzyloxymethyl)-piperazine, 2-hydroxymethyl-piperazine-1-carboxylic acid tert-butyl ester, cyclohexanone, 2-methylcyclohexanone, 3-methylcyclohexanone, 4-phenylcyclohexanone, 4-tert-butylcyclohexanone, 3,3-dimethylcyclohexanone, cis-3,5-dimethylcyclohexanone, cyclopentanone, cycloheptanone are commercially available.

Utility

The NMDA receptor is central to a wide range of CNS processes, and plays a role in a variety of disease states in humans or other species. The action of GlyT1 transporters affects the local concentration of glycine around NMDA receptors. Selective GlyT1 inhibitors slow the removal of glycine from the synapse, causing the level of synaptic glycine to rise. This in turn increases the occupancy of the glycine binding site on the NMDA receptor, which increases activation of the NMDA receptor following glutamate release from the presynaptic terminal. Because a certain amount of glycine is needed for the efficient functioning of NMDA receptors, any change to that local concentration can affect NMDA-mediated neurotransmission. Changes in NMDA-mediated neurotransmission have been implicated in certain neuropsychiatric disorders such as dementia, depression and psychoses, for example schizophrenia, and learning and memory disorders, for example attention deficit disorders and autism.

Accordingly, the compounds of the present invention have utility in treating a variety of neurological and psychiatric disorders associated with glutamatergic neurotransmission dysfunction, including one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, Parkinson's disease, Huntington's disease, Pick's disease, Creutzfeldt-Jacob disease, perinatal hypoxia, other general medical conditions or substance abuse); delirium, amnestic disorders or age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorder; learning disorders, pervasive developmental disorder including autistic disorder, attention disorders including attention-deficit hyperactivity disorder (ADHD) and conduct disorder; NMDA receptor-related disorders such as autism, depression, benign forgetfulness, childhood learning disorders and closed head injury; movement disorders, including akinesias and akinetic-rigid syndromes (including Parkinson's disease, drug-induced parkinsonism, postencephalitic parkinsonism, progressive I supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias [including tremor (such as rest tremor, postural tremor and; intention tremor)], chorea (such as Sydenham's chorea, Huntington's disease, benign hereditary chorea, neuroacanthocytosis, symptomatic chorea, drug-induced chorea and hemiballism), myoclonus (including generalized myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); urinary incontinence; neuronal damage including ocular damage, retinopathy or macular degeneration of the eye, tinnitus, hearing impairment and loss, and brain edema; emesis; and sleep disorders including insomnia and narcolepsy.

Of the disorders above, the treatment of schizophrenia, bipolar disorder, depression including unipolar depression, seasonal depression and post-partum depression, premenstrual syndrome (PMS) and premenstrual dysphoric disorder (PDD), learning disorders, pervasive developmental disorder including autistic disorder, attention disorders including Attention-Deficit/Hyperactivity Disorder, autistic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

In a specific embodiment, the present invention provides a method for treating cognitive disorders, comprising: administering to a patient in need thereof an effective amount of a compound of the present invention. Particular cognitive disorders are dementia, delirium, amnestic disorders and age related cognitive decline. At present, the text revision of the fourth edition of the Diagnostic and Statistical Manual of Mental Disorders (DSM-IV-TR) (2000, American Psychiatric Association, Washington D.C.) provides a diagnostic tool that includes cognitive disorders including dementia, delirium, amnestic disorders and age-related cognitive decline. As used herein, the term "cognitive disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "cognitive disorders" is intended to include like disorders that are described in other diagnostic sources.

In another specific embodiment, the present invention provides a method for treating anxiety disorders, comprising: administering to a patient in need thereof an effective amount of a compound of the present invention. Particular anxiety disorders are generalized anxiety disorder, obsessive-compulsive disorder and panic attack. At present, the text revision of the fourth edition of the Diagnostic and Statistical Manual of Mental Disorders (DSM-IV-TR) (2000, American Psychiatric Association, Washington D.C.) provides a diagnostic tool that includes anxiety disorders as generalized anxiety disorder, obsessive-compulsive disorder and panic attack. As used herein, the term "anxiety disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term 'anxiety disorders" is intended to include like disorders that are described in other diagnostic sources.

In another specific embodiment, the present invention provides a method for treating schizophrenia or psychosis comprising: administering to a patient in need thereof an effective amount of a compound of the present invention. Particular schizophrenia or psychosis pathologies are paranoid, disorganized, catatonic or undifferentiated schizophrenia and substance-induced psychotic disorder. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

In another specific embodiment, the present invention provides a method for treating substance-related disorders and addictive behaviors, comprising: administering to a patient in need thereof an effective amount of a compound of the present invention. Particular substance-related disorders and addictive behaviors are persisting dementia, persisting amnestic disorder, psychotic disorder or anxiety disorder induced by substance abuse, and tolerance of, dependence on or withdrawal, from substances of abuse. At present, the text revision of the fourth edition of the Diagnostic; Statistical Manual of Mental Disorders (DSM-IV-TR) (2000, American Psychiatric Association, Washington D.C.) provides a diagnostic tool that includes persisting dementia, persisting amnestic disorder, psychotic disorder or anxiety disorder induced by substance abuse; and tolerance of, dependence on or withdrawal from substances of abuse. As used herein, the term "substance-related disorders and addictive behaviors" includes treatment of those mental disorders as described in DSM-IV TR. The skilled artisan will recognize that there are alternative nomenclatures, nosologies and classification systems for mental disorders, and that these systems evolve with medical and scientific progress. Thus the term "substance-related disorders and addictive behaviors" is intended to include like disorders that are described in other diagnostic sources.

Testing

The GlyT1 inhibitory activity of the compounds of the present invention can be tested using the in vitro and in vivo assays described in working Example 1 below.

Administration and Pharmaceutical Composition

In general, the compounds of this invention will be administered in a therapeutically effective amount by any of the accepted modes of administration for agents that serve similar utilities. Therapeutically effective amounts of compounds of Formula (I) may range from about 0.01 to about 500 mg per kg patient body weight per day, which can be administered in single or multiple doses. Preferably, the dosage level will be about 0.1 to about 250 mg/kg per day; more preferably about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions are preferably provided in the form of tablets containing about 1.0 to about 1000 milligrams of the active ingredient, particularly about 1.0, 5.0, 10, 15, 20, 25, 50, 75, 100, 150, 200, 250, 300, 400, 500, 600, 750, 800, 900, and 1000 milligrams of the active ingredient. The actual amount of the compound of this invention, i.e., the active ingredient, will depend upon numerous factors such as the severity of the disease to be treated, the age and relative health of the subject, the potency of the compound utilized, the route and form of administration, and other factors.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of formula (I) in combination with at least one pharmaceutically acceptable excipient. Acceptable excipients are non-toxic, aid administration, and do not adversely affect the therapeutic benefit of the compound of formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 18th ed., 1990).

The level of the compound in a formulation can vary within the full range employed by those skilled in the art. Typically, the formulation will contain, on a weight percent (wt %) basis, from about 0.01-99.99 wt % of a compound of formula (I) based on the total formulation, with the balance being one or more suitable pharmaceutical excipients. Preferably, the compound is present at a level of about 1-80 wt %.

The compounds of the present invention may be used in combination with one or more other drugs in the treatment of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is preferred. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly.

Accordingly, the pharmaceutical compositions of the present invention also include those that contain one or more other active ingredients, in addition to a compound of the present invention.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention also include those that also contain one or more other active ingredients, in addition to a compound of the present invention. The weight ratio of the compound of the present invention to the second active ingredient may be varied and will depend upon the effective dose of each ingredient. Generally, an effective dose of each will be used.

In one embodiment, the compound of the present invention may be administered in combination with anti-Alzheimer's agents, beta-secretase inhibitors, gamma-secretase inhibitors, HMG-CoA reductase inhibitors, NSAID's including ibuprofen, vitamin E, and anti-amyloid antibodies. In another embodiment, the compound of the present invention may be administered in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, PDE10 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazopam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, kanylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof.

In another embodiment, the compound of the present invention may be administered in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexol)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and prarnipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the compound of the present invention may be administered in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the compound of the present invention may be administered in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the compound of the present invention may be administered in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNR1s), corticotropin releasing factor (CRF) antagonists, adrenoreceptor antagonists, neurokinin-1 receptor antagonists, atypical antidepressants, benzodiazepines, 5-HTA agonists or antagonists, especially 5-HTA partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide, venlafaxine; duloxetine; aprepitant; bupropion, lithium, nefazodone, trazodone and viloxazine; alprazolam, chlordiazepoxide, clonazepam, chlorazepate, diazopam, halazepam, lorazepam, oxazopam and prazepam; buspirone, flesinoxan, gepirone and ipsapirone, and pharmaceutically acceptable salts thereof.

EXAMPLES

The following preparations of compounds of Formula (I) and intermediates (References) are given to enable those skilled in the art to more clearly understand and to practice the present invention. They should not be considered as limiting the scope of the invention, but merely as being illustrative and representative thereof.

Synthetic Examples

Example 1

Synthesis of 2-((R)-2-methyl-4-(6,7,8,9-tetrahydro-5H-benzo[7]annulen-5-yl)-piperazin-1-yl)acetic acid

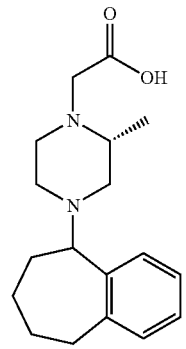

Step 1

A mixture of 1-benzosuberone (0.803 ml, 5.01 mmol), (R)-2-methylpiperazine (1.505 g, 15 mmol) in titanium (4+) isopropoxide (4.399 ml, 15 mmol) was heated at 80° C. overnight. After cooling to RT, the reaction mixture was diluted with 30 mL of MeOH and sodium borohydride (0.529 ml, 15 mmol) was slowly added. After stirring at rt for 20 min, the solvent was evaporated to dryness. The residue was redissolved in 50 mL of EtOAc and to this solution was added 10 g of NaHCO$_3$ and 0.5 mL of water to generate a white slurry. After stirring at rt for 2 h, the mixture was filtered with the help of excess EtOAc and the filtrate was evaporated to dryness. Column chromatography (SiO$_2$, DCM/MeOH=100:5 to 100:10 to 100:15 to 100:20) gave (3R)-3-methyl-1-(6,7,8,9-tetrahydro-5H-benzo[7]annulen-5-yl)piperazine (860 mg, 70% yield) as an off white gum.

Step 2

To a solution of (3R)-3-methyl-1-(6,7,8,9-tetrahydro-5H-benzo[7]annulen-5-yl)piperazine (620 mg, 2.537 mmol) in MeCN was added methyl 2-bromoacetate (466 mg, 3.044 mmol) followed by diisopropylethylamine (0.884 ml, 5.074 mmol). The reaction mixture was stirred at rt for 5 h. The solvent was evaporated under high vacuum and the residue was loaded on column (SiO$_2$, hexane to hexane/EtOAc=100:10 to 100:20 to 100:30 to 100:40) to give methyl 2-((R)-2-methyl-4-(6,7,8,9-tetrahydro-5H-benzo[7]annulen-5-yl)piperazin-1-yl)acetate (800 mg, 99.6% yield) as a gum.

Step 3

To methyl 2-((R)-2-methyl-4-(6,7,8,9-tetrahydro-5H-benzo[7]annulen-5-yl)piperazin-1-yl)acetate (420 mg, 1.327 mμmol) in 14 mL of MeOH/THF/H$_2$O (3:3:1) was added lithium hydroxide monohydrate (195 mg, 4.645 mmol). After stirring at rt for 3 h when HPLC-MS showed complete conversion, the solvent was evaporated to dryness under high vacuum. The residue was redissolved in water and the solution was adjusted to PH=4 with 2 N HCl, extracted with DCM, dried over Na$_2$SO$_4$, filtered and evaporated to dryness. Column chromatography (SiO$_2$, DCM to DCM/MeOH=100:10 to 100:20 to 100:30) gave 2-((R)-2-methyl-4-(6,7,8,9-tetrahydro-5H-benzo[7]annulen-5-yl)piperazin-1-yl)acetic acid (360 mg, 89.7% yield) as a white solid. MS (ESI, pos. ion) m/z: 303.2 (M+1).

Example 2

Synthesis of 2-((R)-2-methyl-4-(2-phenylcyclohexyl)piperazin-1-yl)acetic acid dihydrochloride

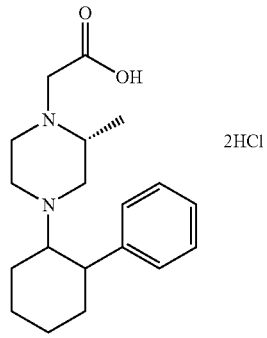

Step 1

A mixture of 2-phenylcyclohexanone (1.74 g, 9.99 mmol), (R)-2-methylpiperazine (3.00 g, 30.0 mmol) and titanium (4+) isopropoxide (5.85 ml, 20.0 mmol) was heated at 80° C. under N$_2$ overnight. After cooling to rt, 10 mL of MeOH was added followed by slow addition of NaBH$_4$ (1.13 g, 30.0 mmol). After stirring for 30 min, the solvent was evaporated and the residue was redissolved in EtOAc. The solution was treated with 15 g of NaHCO$_3$ and 1 mL of water to generate slurry. This was filtered with large excess of EtOAc. The solvent was evaporated and the residue was submitted to flash chromatography (SiO$_2$, DCM to DCM/MeOH=100:5 to 100:10 to 100:20) to give (3R)-3-methyl-1-(2-phenylcyclohexyl)-piperazine (1.82 g, 70.5% yield) as a colorless oil.

Step 2

To a solution of (3R)-3-methyl-1-(2-phenylcyclohexyl)piperazine (900 mg, 3.48 mmol) (crude) in MeCN was added tert-butyl 2-bromoacetate (0.815 g, 4.18 mmol) followed by diisopropylethylamine (1.21 ml, 6.97 mmol). The reaction was stirred at RT for 5 h. The solvent was evaporated under high vacuum and the residue was loaded on column (SiO$_2$, hexane to hexane/EtOAc=100:10 to 100:20 to 100:30 to 100:40) to give tert-butyl 2-((R)-2-methyl-4-(2-phenylcyclohexyl)piperazin-1-yl)acetate (1.16 g, 89.4% yield) as a gum.

Step 3

A mixture of tert-butyl 2-((R)-2-methyl-4-(2-phenylcyclohexyl)piperazin-1-yl)acetate (430 mg, 1.154 mmol) in 3 mL of 37% HCl was stirred at 50 C for 3 h. After LCMS showed complete conversion to the product, the solution was evaporated under high vacuum to dryness. The residue was crashed out of diethyl ether and dried to give 2-((R)-2-methyl-4-(2-phenylcyclohexyl)piperazin-1-yl)acetic acid dihydrochloride (440 mg, 97.9% yield) as an off white solid. MS (ESI, pos. ion) m/z: 317.2 (M+1).

The following analogs were prepared using similar procedure:

2-((R)-4-(6-methoxy-1,2,3,4-tetrahydronaphthalen-1-yl)-2-methylpiperazin-1-yl)acetic acid;
2-((R)-4-(6-bromo-2,3-dihydro-1H-inden-1-yl)-2-methylpiperazin-1-yl)acetic acid; and
2-((R)-4-(5-bromo-2,3-dihydro-1H-inden-1-yl)-2-methylpiperazin-1-yl)acetic acid.

Example 3

Synthesis of 2-(4-(phenyl(3-(trifluoromethyl)phenyl)amino)piperidin-1-yl)acetic acid

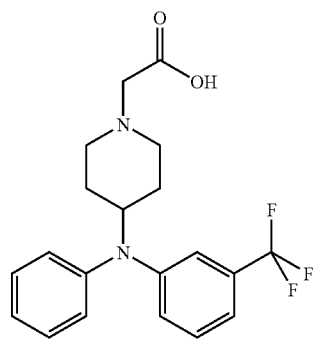

Step 1

To a solution of Boc-4-piperidone (4.0 g, 20 mmol), aniline (1.9 ml, 20 mmol), and acetic acid, glacial (1.4 ml, 24 mmol) in dichloroethane (60 mL) was added sodium triacetoxyborohydride (6.0 g, 28 mmol) portionwise at RT. The suspension was stirred at RT for 24 h, diluted with water and extracted with dichloromethane. The organic layer was dried over Na₂SO₄ and concentrated. The residue was purified by ISCO using 0-30% EtOAc in Hexanes to give tert-butyl 4-(phenylamino)piperidine-1-carboxylate (2.5 g, 45% yield).
Step 2

A mixture of tert-butyl 4-(phenylamino)piperidine-1-carboxylate (2.30 g, 8 mmol), 1-iodo-3-(trifluoromethyl)benzene (1 ml, 8 mmol), palladium(ii) acetate (0.07 g, 0.3 mmol), rac-2,2'-bis(diphenylphosphino)-1,1'-binaphthyl (0.2 g, 0.3 mmol), and potassium tert-butoxide, 1.0M solution in tetrahydrofuran (1 ml, 10 mmol) in toluene (20 mL) was heated at 110° C. for 18 h. The reaction mixture was diluted with EtOAc, filtered, washed with 1N NaOH and brine, and the organic layer was concentrated under vacuum. Conc HCl (20 mL) was added to the residue and the solution was concentrated under vacuum. Conc HCl (20 mL) was added to the residue and the solution was stirred at RT for 8 h and concentrated. The pH was adjusted to 11 with the addition of 1N NaOH solution and the product was extracted with DCM. The DCM layer was dried (Na₂SO₄) and concentrated under reduced pressure. The residue was purified with ISCO using 0-15% MeOH in DCM to give product N-phenyl-N-(3-(trifluoromethyl)phenyl)piperidin-4-amine (1.5 g, 56% yield).
Step 3

To solution of N-phenyl-N-(3-(trifluoromethyl)phenyl)piperidin-4-amine (1.3 g, 4.1 mmol) in MeCN (15 mL) was added ethyl bromoacetate (0.50 ml, 4.5 mmol) followed by triethylamine (1.1 ml, 8.1 mmol). The reaction mixture was stirred at RT for 4 h, diluted with water and extracted with DCM. The combined DCM layer was dried (Na₂SO₄), and concentrated. The product was purified with ISCO using 0-15% EtOAc in DCM to give ethyl 2-(4-(phenyl(3-(trifluoromethyl)phenyl)amino)piperidin-1-yl)acetate (1.2 g, 73% yield).
Step 4

A solution of ethyl 2-(4-(phenyl(3-(trifluoromethyl)phenyl)amino)piperidin-1-yl)-acetate (1.1 g, 3 mmol) and sodium hydroxide 1N (4 ml, 4 mmol) in MeOH (15 mL) was heated to 70° C. with stirring for 2 h. Upon cooling to RT, the solvent was removed under reduced pressure. The residue was dissolved in water and the pH adjusted to 4 with 2 N HCl. The solution was extracted with DCM. The DCM layers were combined, dried (Na₂SO₄), and concentrated. The residue was purified with ISCO using 0-15% MeOH in DCM to give 2-(4-(phenyl(3-(trifluoromethyl)phenyl)amino)piperidin-1-yl)acetic acid (0.8 g, 78% yield). MS (ESI, pos. ion) m/z: 379.1 (M+1).
The following analogs were prepared using similar procedure:
2-(3-((3-bromophenyl)(phenyl)amino)pyrrolidin-1-yl) acetic acid, 2-(3-(phenyl(3-(pyridin-3-yl)phenyl)amino)pyrrolidin-1-yl)acetic acid, and 2-(3-(diphenylamino)-pyrrolidin-1-yl)acetic acid were made from tert-butyl 3-oxopyrrolidine-1-carboxylate and appropriate anilines and aryl bromides;
2-(3-(phenyl(4-(trifluoromethyl)phenyl)amino)pyrrolidin-1-yl)acetic acid;
2-(3-(phenyl(4-(trifluoromethyl)phenyl)amino)piperidin-1-yl)acetic acid;
2-(3-(phenyl(3-(trifluoromethyl)phenyl)amino)piperidin-1-yl)acetic acid;
2-(4-(diphenylamino)-2-methylpiperidin-1-yl)acetic acid;
2-(4-(phenyl(4-(trifluoromethyl)phenyl)amino)piperidin-1-yl)acetic acid;
2-(2-methyl-4-(phenyl(4-(trifluoromethyl)phenyl)amino)piperidin-1-yl)acetic acid; and
2-(2-methyl-4-(phenyl(3-(trifluoromethyl)phenyl)amino)piperidin-1-yl)acetic acid.

Example 4

Synthesis of 2-(3-(phenyl(4-(trifluoromethyl)phenyl) methyl)piperidin-1-yl)acetic acid

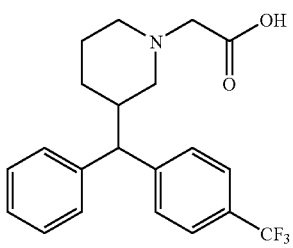

Step 1

To a solution of phenyl(4-(trifluoromethyl)phenyl)methanone (1.5 g, 6.0 mmol) and tert-butyl 3-oxopiperidine-1-carboxylate (1.3 g, 6.5 mmol) in THF (20 mL) was added Zn (1.8 g, 28.5 mmol) and the resulting mixture was stirred at rt for 10 min and was then cooled to 0° C. To this was added TiCl₄ (1.4 mL, 13.5 mmol) dropwise. The reaction mixture was stirred first at rt for 15 min and then at 50° C. for 4 h. The solvent was removed under vacuum. Then it was cooled to 0-5° C. and added 2N HCl solution and extracted with ethyl acetate. The combined organic layer was washed with K₂CO₃ solution, dried over anhydrous sodium sulfate and concentrated under vacuum to afford the crude product. It was cooled to 0-5° C., pentane was added and stirred for 30 min and dried under vacuum to afford 3-(phenyl(4-(trifluoromethyl)phenyl)methylene)piperidine (1.1 g, 57% yield) as a grey solid. MS (ESI, pos. ion) m/z: 318 (M+1).
Step 2

To a solution of 3-(phenyl(4-(trifluoromethyl)phenyl)methylene)piperidine (1.0 g, 3.15 mmol) in methanol (25 mL) was charged with Pd/C under nitrogen atmosphere and fitted with hydrogen balloon using stopcock and covered with Teflon. The reaction mixture was stirred under hydrogen atmosphere for 8 h. It was filtered through celite, the celite was washed with methanol, and the solvent was removed under reduced pressure to afford the crude product which was then crashed out of pentane to give pure 3-(phenyl(4-(trifluoromethyl)phenyl)-methyl)piperidine (1.0 g, 98% yield) as a grey oil. MS (ESI, pos. ion) m/z: 320 (M+1).
Step 3

To a solution of 3-(phenyl(4-(trifluoromethyl)phenyl)methyl)piperidine (1.0 g, 3.13 mmol) in MeCN (10 mL) was added triethyl amine (1.3 mL, 9.4 mmol) at rt. After stirring at rt for 15 min, it was cooled to 0° C. and ethyl bromoacetate (0.62 g, 3.71 mmol) was added dropwise. After stirring at rt for 6 h, the solvent was removed under vacuum and the residue was diluted with water, extracted with ethyl acetate, the combined organic layer was dried over anhydrous sodium sulfate and concentrated under vacuum to afforded the crude product. Column chromatography (SiO₂, 10-15% ethyl acetate in hexane) afforded ethyl 2-(3-(phenyl(4-(trifluoromethyl)phenyl)methyl)piperidin-1-yl)acetate (0.6 g, 48% yield) as a pale yellow solid. MS (ESI, pos. ion) m/z: 406 (M+1).

Step 4

To a solution of ethyl 2-(3-(phenyl(4-(trifluoromethyl)phenyl)methyl)piperidin-1-yl)acetate (0.5 g, 1.23 mmol) in THF/MeOH/water (12 mL, 7:3:2) at 5° C. was added LiOH.H$_2$O (0.15 g, 3.7 mmol). After stirring at rt for 4 h, the solvent was removed under vacuum. The residue was diluted with water and the pH was adjusted to 4 with diluted HCl, extracted with ethyl acetate, and the combined organic layer was dried over anhydrous sodium sulfate and concentrated under vacuum. The residue was dissolved in ethyl acetate and crashed out of pentane at cool condition to afford pure 2-(3-(phenyl(4-(trifluoromethyl)-phenyl)methyl)piperidin-1-yl)acetic acid (0.3 g, 65% yield) as an off white solid. MS (ESI, pos. ion) m/z: 378 (M+1).

The following analogs were prepared using similar procedure:

2-(4-benzhydryl-2-methylpiperidin-1-yl)acetic acid;
2-(2-methyl-4-(phenyl(3-(trifluoromethyl)phenyl)methyl)piperidin-1-yl)acetic acid;
2-(2-methyl-4-(phenyl(4-(trifluoromethyl)phenyl)methyl)piperidin-1-yl)acetic acid;
2-(3-(phenyl(3-(trifluoromethyl)phenyl)methyl)piperidin-1-yl)acetic acid; and
2-(3-(phenyl(4-(trifluoromethyl)phenyl)methyl)pyrrolidin-1-yl)acetic acid.

Example 5

Synthesis of 2-(4-(phenyl(4-(trifluoromethyl)phenyl)methyl)piperidin-1-yl)acetic acid

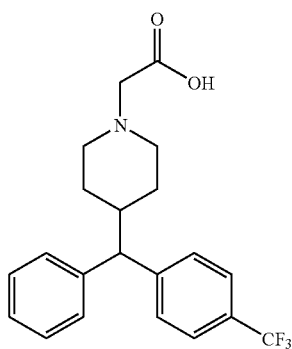

Step 1

To a solution of 1-(tert-butoxycarbonyl)piperidine-4-carboxylic acid (11 g, 48 mmol) in DCM (120 mL) was added CDI (11 g). After stirring at rt for 2 h, N,O-dimethylhydroxylamine hydrochloride was added in portions. The mixture was stirred for 3 h at rt and was then left to stand overnight. The solvent was removed under vacuum, the residue was extracted with DCM, washed with brine and water, dried over anhydrous sodium sulfate and concentrated to give crude tert-butyl 4-(methoxy(methyl)carbamoyl)piperidine-1-carboxylate (8 g, 61% yield) as a white solid which was used directly in the next step.

Step 2

To a solution of tert-butyl 4-(methoxy(methyl)carbamoyl)piperidine-1-carboxylate (8.0 g, 29.4 mmol) in THF (25 mL) was added PhMgCl (8.0 g, 58.8 mmol) dropwise at 0° C. After stirring at rt for 2 h, the reaction was quenched with ammonium chloride solution and extracted with ethyl acetate, dried over anhydrous sodium sulfate and concentrated under vacuum to afford tert-butyl 4-benzoylpiperidine-1-carboxylate (5 g, 59% yield) as a pale yellow solid which was used directly in the next step.

Step 3

To a solution of 1-iodo-4-(trifluoromethyl)benzene (0.92 g, 3.4 mmol) in dry THF at −78° C. was added n-BuLi (3 mL, 1.6 M in hexane) dropwise and the mixture was stirred at the same temperature for 30 min. To this was added a solution of tert-butyl 4-benzoylpiperidine-1-carboxylate (1.0 g, 3.4 mmol) in minimum amount of dry THF dropwise and the resulting reaction mixture was allowed to warm up to rt over 2 h. The reaction was quenched with ammonium chloride solution, extracted with ethyl acetate, dried over anhydrous sodium sulfate and concentrated to afford tert-butyl 4-(hydroxy(phenyl)(4-(trifluoromethyl)phenyl)methyl)-piperidine-1-carboxylate (1.0 g, 66% yield) as a pale yellow solid which was used in the next step without further purification.

Step 4

To a solution of tert-butyl 4-(hydroxy(phenyl)(4-(trifluoromethyl)phenyl)methyl)piperidine-1-carboxylate (1.0 g, 2.29 mmol) in dry DCM (10 mL) at 0° C. was added TFA (10 mL) dropwise and the resulting solution was stirred at rt for 16 h. The solvents were removed under vacuum. The residue was diluted with DCM, washed with sodium bicarbonate solution and water, dried over sodium sulfate and concentrated under vacuum to afford crude compound which was crashed out of pentane to give 4-(phenyl(4-(trifluoromethyl)phenyl)-methylene)piperidine (0.5 g, 69%) as a grey solid. MS (ESI, pos. ion) m/z: 318 (M+1).

Step 5

To a solution of 4-(phenyl(4-(trifluoromethyl)phenyl)methylene)piperidine (0.5 g, 1.57 mmol) in MeOH (15 mL) was added Pd/C (0.1 g) and the mixture was stirred in hydrogen at 3 atmospheric pressure for 12 h. It was filtered through silica gel pad, washed with MeOH and concentrated to give crude 4-(phenyl(4-(trifluoromethyl)phenyl)methyl)piperidine (0.5 g, 98% yield) as a grey solid which was used in the next step without further purification. MS (ESI, pos. ion) m/z: 320 (M+1).

Step 6

To a solution of 4-(phenyl(4-(trifluoromethyl)phenyl)methyl)piperidine (0.4 g, 1.25 mmol) in MeCN (15 mL) was added triethyl amine (0.45 mL, 3.2 mmol) at rt. After stirring at rt for 10 min, it was cooled to 0° C. and ethyl bromoacetate (0.27 mL, 1.62 mmol) was added dropwise. After stirring at rt for 16 h, the solvent was removed under vacuum and the residue was diluted with water, extracted with ethyl acetate, the combined organic layer was dried over anhydrous sodium sulfate and concentrated under vacuum to afforded the crude product. Column chromatography (SiO2, 5-10% ethyl acetate in hexane) afforded ethyl 2-(4-(phenyl(4-(trifluoromethyl)phenyl)methyl)piperidin-1-yl)acetate (0.25 g, 52% yield) as a pale yellow solid. MS (ESI, pos. ion) m/z: 406 (M+1).

Step 7

To a solution of ethyl 2-(4-(phenyl(4-(trifluoromethyl)phenyl)methyl)piperidin-1-yl)acetate (0.2 g, 0.49 mmol) in THF/MeOH (10 mL, 1:1) was added LiOH.H$_2$O (0.15 g, 3.7 mmol). After stirring at rt for 4 h, the solvent was removed under vacuum. The residue was diluted with water and the pH was adjusted to 3 with diluted HCl, extracted with DCM, and the combined organic layer was dried over anhydrous sodium sulfate and concentrated under vacuum to afford pure 2-(4-(phenyl(4-(trifluoromethyl)phenyl)methyl)piperidin-1-yl)acetic acid (0.07 g, 36% yield) as a white solid. MS (ESI, pos. ion) m/z: 378 (M+1).

The following analogs were prepared using similar procedure:
2-(4-(phenyl(3-(trifluoromethyl)phenyl)methyl)piperidin-1-yl)acetic acid; and
2-(4-(phenyl(2-(trifluoromethyl)phenyl)methyl)piperidin-1-yl)acetic acid.

Example 6

Synthesis of 2-(3-(phenyl(m-tolyl)methyl)pyrrolidin-1-yl)acetic acid

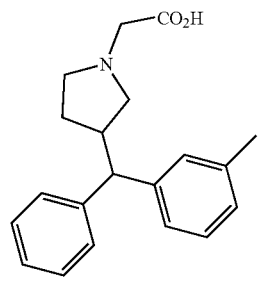

Step 1

To a mixture of 2-methylbenzophenone (2.0 g, 10.2 mmol) and N-boc-3-pyrrolidone (1.89 g, 10.2 mmol) in THF was added zinc powder (3.3 g, 59 mmol) at 10-15° C. and stirred for 15 min. To the reaction mixture was added $TiCl_4$ (4.76 g, 25 mmol) and the contents were brought to 60° C. and stirred for 8 h. The reaction mixture was allowed to cool to room temperature, diluted HCl was added and extracted with EtOAc. The organic layer was washed with aqueous sodium potassium tartarate solution. The organic layer was dried over anhydrous sodium sulfate and concentrated under reduced pressure to afford the crude product which was washed with n-hexane to afford 1.8 g of (Z)-3-(phenyl(m-tolyl)methylene)pyrrolidine.

Step 2

To a solution of (Z)-3-(phenyl(m-tolyl)methylene)pyrrolidine (4.0 g, 16.1 mmol) in methanol (40 mL) at room temperature was added 10% Pd/C (9.5 g) and the contents were hydrogenated at 50 psi hydrogen atmosphere and at room temperature for 12 h. The reaction mixture was filtered through celite bed and the bed was washed with methanol. The filtrate was concentrated under reduced pressure to afford 3.0 g of 3-(phenyl(m-tolyl)methyl)pyrrolidine.

Step 3

A solution of 3-(phenyl(m-tolyl)methyl)pyrrolidine (3.0 g, 12 mmol) and triethylamine (1.8 mL, 12.9 mmol) in dichloromethane (30 mL) was stirred at 0° C. for 10 min, and then methylbromoacetate (1.5 mL, 15.8 mmol) was added dropwise. After stirring the reaction mixture at 0° C. for 3 h, reaction mixture was warmed to room temperature and concentrated under reduced pressure. To the residue was added water and the aqueous layer was extracted with dichloromethane. The organic layer was dried over anhydrous sodium sulfate and concentrated under reduced pressure to afford the crude product. The crude product was dissolved in dichloromethane and precipitated with diethyl ether to afford 1.6 g of methyl 2-(3-(phenyl(m-tolyl)methyl)pyrrolidin-1-yl)acetate.

Step 4

To a solution of methyl 2-(3-(phenyl(m-tolyl)methyl)pyrrolidin-1-yl)acetate (1.5 g, 4.64 mmol) in THF at 0° C. was added a solution of lithium hydroxide (0.58 g, 13.8 mmol) in water and the reaction mixture was stirred for 4 h. The reaction mixture was concentrated under reduced pressure. To the residue was added water, the pH of the aqueous layer was adjusted to 3 using dil.HCl and extracted with 30% methanol in chloroform. The organic layer was dried over anhydrous sodium sulfate and concentrated under reduced pressure to afford 0.72 g of the title compound.

Similarly, 2-(3-benzhydrylpyrrolidin-1-yl)acetic acid was prepared from benzophenone.

Example 7

Synthesis of (R)-2-(4-(1-(4-chlorophenyl)cyclohexyl)-2-methylpiperazin-1-yl)acetic acid

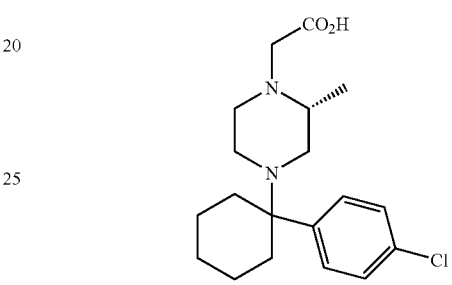

Step 1

To a solution of (R)-2-methylpiperazine (10 g, 100 mmol) in ethanol at room temperature was added $K_2CO_3$ (27.6 g, 200 mmol). The reaction mixture was cooled to 0° C., benzyl bromide (15.3 g, 89.5 mmol) was added and the reaction mixture was heated to 60° C. and stirred for 8 h. The reaction mixture was allowed to cool to room temperature, filtered through a filtration funnel and the filtrate was concentrated under reduced pressure to remove ethanol. The residue was washed with water and extracted with dichloromethane. The organic layer was dried over anhydrous sodium sulfate and concentrated under reduced pressure to afford crude product. The crude product was purified by silica gel (100-200 mesh) column chromatography eluting with 5% methanol in chloroform to afford pure 12.0 g of (R)-1-benzyl-3-methylpiperazine.

Step 2

To a solution of (R)-1-benzyl-3-methylpiperazine (10 g, 52.6 mmol) in dichloromethane (30 mL) at room temperature was added triethylamine (10.6 g, 106 mmol) and the reaction mixture was stirred for 1 h. To the reaction mixture was added $(BOC)_2O$ (13.7 g, 62.8 mmol) and the contents were stirred for further 4 h. The reaction mixture was quenched in water and extracted with dichloromethane. The organic layer was dried over anhydrous sodium sulfate and concentrated under reduced pressure to afford the crude product. The crude product was purified by silica gel (100-200 mesh) column chromatography eluting with 10% ethyl acetate in n-hexanes to afford 13.0 g of (R)-tert-butyl 4-benzyl-2-methylpiperazine-1-carboxylate.

Step 3

To a solution of (R)-tert-butyl 4-benzyl-2-methylpiperazine-1-carboxylate (10 g, 34.5 mmol) in methanol (100 mL) was added Pd/C (1.0 g) and the reaction mixture was subjected to hydrogenolysis under balloon pressure of hydrogen, at room temperature for 8 h. The reaction mixture was filtered through celite bed and the bed was washed with methanol.

The filtrate was concentrated under reduced pressure to afford the crude product which was purified by silica gel (100-200 mesh) column chromatography eluting with 5% methanol in chloroform to afford 4.8 g of (R)-tert-butyl 2-methylpiperazine-1-carboxylate.

Step 4

To a solution of (R)-tert-butyl 2-methylpiperazine-1-carboxylate (3.5 g, 17.5 mmol) in water (20 mL) at 0° C. were added acetic acid (2 mL) and cyclohexanone (1.7 g, 12.3 mmol). To the reaction mixture at room temperature was added KCN (1.7 g, 2.62 mmol) and stirred for 20 h. The reaction mixture was quenched in ice water and extracted with ethyl acetate. The organic layer was dried over anhydrous sodium sulfate and concentrated under reduced pressure to afford 3.0 g 1-(4-chlorophenyl)cyclohexanecarbonitrile which was used in the next step without further purification.

Step 5

To a solution of 1-(4-chlorophenyl)cyclohexanecarbonitrile (2.1 g, 9.6 mmol) in THF (15 mL) at room temperature was added (4-chlorophenyl)magnesium bromide (21 mmol, 21 mL of 1M in ether) slowly under nitrogen atmosphere. The reaction mixture was stirred at room temperature for 16 h. The reaction mixture was quenched with aqueous ammonium chloride solution and extracted with ethyl acetate. The organic layer was dried over anhydrous sodium sulfate and concentrated under reduced pressure to afford the crude product. It was purified by silica gel (100-200 mesh) column chromatography eluting with 5% ethyl acetate in n-hexanes to afford 0.4 g of (R)-tert-butyl 4-(1-(4-chlorophenyl)cyclohexyl)-2-methylpiperazine-1-carboxylate.

Step 6

To a solution of (R)-tert-butyl 4-(1-(4-chlorophenyl)cyclohexyl)-2-methylpiperazine-1-carboxylate (0.80 g, 2.03 mmol) in 1,4-dioxane (5 mL) at 0° C. was added dropwise a saturated solution dioxane-HCl (4 mL). The reaction mixture was warmed to room temperature and stirred for 2 h. The reaction mixture was concentrated under reduced pressure and the residue was washed with ethyl acetate. The pH of the residue was adjusted to 7 using aqueous 10% sodium carbonate solution and extracted with ethyl acetate. The organic layer was dried over anhydrous sodium sulfate and concentrated under reduced pressure to afford 0.5 g of (R)-1-(1-(4-chlorophenyl)cyclohexyl)-3-methylpiperazine.

Step 7

To a solution of (R)-1-(1-(4-chlorophenyl)cyclohexyl)-3-methylpiperazine (0.6 g, 2.05 mmol) in dichloromethane at room temperature were added methyl glyoxalate (0.23 g, 2.61 mmol), acetic acid (0.18 g, 3 mmol) and Na(OAc)$_3$BH (1.08 g, 5.1 mmol). The reaction mixture was stirred at room temperature for 12 h. The reaction mixture was diluted with water and extracted with ethyl acetate. The organic layer was dried over anhydrous sodium sulfate and concentrated under reduced pressure to afford the crude product. It was purified by silica gel (100-200 mesh) column chromatography eluting with ethyl acetate in n-hexanes to afford 0.49 g of (R)-methyl 2-(4-(1-(4-chlorophenyl)cyclohexyl)-2-methyl-piperazin-1-yl)acetate.

Step 8

To a solution of (R)-methyl 2-(4-(1-(4-chlorophenyl)cyclohexyl)-2-methyl-piperazin-1-yl)acetate (0.5 g, 1.37 mmol) in THF (10 mL) and methanol (1 mL) at 0° C. was added a solution of LiOH.H$_2$O (0.16 g, 3.81 mmol) in water (1 mL). The reaction mixture was stirred for 4 h. Methanol and THF were distilled under reduced pressure and the residue was washed with ethyl acetate. The pH of the aqueous layer was adjusted to 7 and extracted with ethyl acetate. The organic layer was dried over anhydrous sodium sulfate and concentrated under reduced pressure to afford the crude product which was purified by silica gel (100-200 mesh) column chromatography eluting with 5-7% methanol in chloroform to afford pure (R)-2-(4-(1-(4-chlorophenyl)cyclohexyl)-2-methylpiperazin-1-yl)acetic acid.

The following analogs were prepared using similar procedure:

2-(4-(1-phenylcyclohexyl)piperazin-1-yl)acetic acid;
(R)-2-(2-methyl-4-(1-phenylcyclohexyl)piperazin-1-yl)acetic acid; and
(R)-2-(2-methyl-4-(1-(3-(trifluoromethyl)phenyl)cyclohexyl)piperazin-1-yl)acetic acid.

Biological Examples

Example 1

Glycine Transporter 1 (GlyT1) Uptake Assay

In Vitro:

This cell-based assay measures the ability of test compounds to inhibit the uptake of glycine by the glycine transporter type 1. Human placental choriocarcinoma (JAR) cells endogenously expressing human glycine transporter type 1 (Gly-T1) were used for this assay. For uptake assays, JAR cells were cultured in 96-well cytostar T scintillating microplates (Amersham Biosciences) in RPMI 1640 medium containing 10% fetal bovine serum in the presence of penicillin (100 μg/ml) and streptomycin (100 μg/ml). Cells were plated at a density of $4 \times 10^4$ cells/well and grown at 37° C. in a humidified atmosphere of 5% $CO_2$ for 24 h.

Culture medium was removed from Cytostar plate and JAR cells were incubated with 30 μl of Uptake buffer (120 mM NaCl, 2 mM KCl, 1 mM $CaCl_2$, 1 mM $MgCl_2$, 10 mM Hepes, 5 mM alanine, pH 7.5) with or without compound for 5 min. Then 30 μl of [$^{14}$C] glycine (101 mCi/mmol, obtained from PerkinElmer) diluted in Uptake buffer was added to each well to give a final concentration of 5 μM. After incubation at room temperature for the desired time usually 1-2 h, sealed 96-well Cytostar plates were counted on a TopCount (Packard). Non-specific uptake of [$^{14}$C] glycine was determined in the presence of 10 μM cold ALX-5407 (Sigma).

$IC_{50}$ curves were generated from the raw data collected from the TopCount and fitted with a four-parameter logistic equation using in-house data analysis tool, Activity Base.

In approximate $IC_{50}$ value of a representative number of compounds of Formula (I) in this assay is provided in the table below.

| Table No | Cpd No | $IC_{50}$ μm |
|---|---|---|
| I | 1 | 0.258 |
| I | 3 | 1.01 |
| I | 5 | 0.147 |
| I | 6 | 1.128 |
| I | 7 | 0.393 |
| I | 8 | 0.536 |
| I | 9 | >10 |
| I | 10 | 0.953 |
| I | 11 | >10 |
| I | 12 | 0.687 |
| I | 13 | >10 |
| I | 14 | 1.531 |
| I | 15 | 0.052 |
| I | 16 | 3.519 |
| I | 26 | 0.101 |

-continued

| Table No | Cpd No | IC$_{50}$ μm |
|---|---|---|
| I | 28 | >10 |
| I | 30 | 5.32 |
| I | 22 | 0.129 |
| II | 1 | 0.562 |
| II | 3 | 0.296 |
| II | 4 | >2 |
| II | 5 | 0.018 |
| II | 10 | 0.014 |

In Vivo Assay:

Male Sprague-Dawley rats (250-300 grams) are treated with GlyT1 inhibitor at doses ranging between 1 and 100 mg/kg by oral gavage. Two hours after acute compound administration, CSF are collected and subsequently analyzed for glycine content using HPLC coupled to a fluorescent detector (ESA inc, Chelmsford Mass.).

Formulation Examples

The following are representative pharmaceutical formulations containing a compound of Formula (I).

Tablet Formulation

The following ingredients are mixed intimately and pressed into single scored tablets.

| Ingredient | Quantity per tablet mg |
|---|---|
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
|---|---|
| compound of this invention | 200 |
| lactose spray dried | 148 |
| magnesium stearate | 2 |

Injectable Formulation

Compound of the invention (e.g., compound 1) in 2% HPMC, 1% Tween 80 in DI water, pH 2.2 with MSA, q.s. to at least 20 mg/mL.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed:

1. A compound represented by the formula:

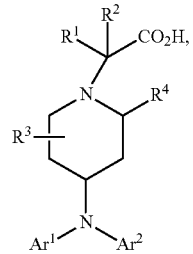

wherein;
R$^1$ and R$^2$ are independently hydrogen or alkyl;
R$^3$ is independently hydrogen or alkyl;
and R$^4$ is methyl; and
Ar$^1$ and Ar$^2$ are independently aryl, or cycloalkyl, where each of the aforementioned ring is optionally substituted with R$^a$, R$^b$ or R$^c$ where R$^a$ is alkyl, halo, haloalkyl, haloalkoxy, alkylthio, cyano, alkoxy, amino, monosubstituted amino, disubstituted sulfonyl, acyl, carboxy, alkylcarbonyl, hydroxyalkyl, alkoxyalkyl, hydroxyalkoxy, alkoxyalkoxy, aminoalkoxy, aminosulfonyl, aminocarbonyl, or acylamino and R$^b$ and R$^c$ are independently selected from alkyl, halo, haloalkyl, haloalkoxy, alkylthio, cyano, alkoxy, monosubstituted amino, disubstituted amino, sulfonyl, acyl, carboxy, alkoxycarbonyl, hydroxyalkyl, alkoxyalkyl, aminoalkyl, hydroxyalkoxy, alkoxyaloxy, aminoalkoxy, aminosulfonyl, aminocarbonyl, acylamino, aryl, heteroaryl, cycloalkyl, or heterocyclyl where the aromatic or alicyclic ring in R$^a$, R$^b$ and R$^c$ is optionally substituted with R$^d$, R$^e$ or R$^f$ which are independently selected from alkyl, halo, haloalkyl, haloalkoxy, alkylthio, cyano, alkoxy, amino, monosubstituted amino, disubstituted amino, sulfonyl, acyl, carboxy, alkoxycarbonyl, hydroxyalkyl, alkoxyalkyl, aminoalkyl, hydroxyalkoxy, alkoxyalkoxy, aminoalkoxy, aminosulfonyl, aminocarbonyl, or acylamino.

2. The compound of claim 1 where R$^1$ and R$^2$ are hydrogen.

3. The compound of claim 1 wherein R$^3$ is hydrogen.

4. The compound of claim 2 wherein R$^3$ is hydrogen.

5. The compound of claim 2 wherein R$^3$ is hydrogen and R$^4$ is alkyl and is located at the carbon atom ortho to the nitrogen substituted with the —CR$^1$R$^2$CO$_2$H group.

6. The compound of claim 1 wherein Ar$^1$ and Ar$^2$ are phenyl.

7. The compound of claim 1 wherein Ar$^1$ is phenyl and Ar$^2$ is phenyl substituted with R$^a$ where R$^a$ is alkyl, halo, haloalkyl, haloalkoxy, cyano, five or six membered heterocyclyl, or five or six membered heteroaryl ring.

8. The compound of claim 1 wherein Ar$^1$ is phenyl and Ar$^2$ is phenyl substituted with R$^a$ where R$^a$ is alkyl, halo, haloalkyl, haloalkoxy, cyano, five or six membered heterocyclyl, or five or six membered heteroaryl ring.

9. The compound of claim 5 wherein $Ar^1$ is phenyl and $Ar^2$ is phenyl substituted with $R^a$ where $R^a$ is alkyl, halo, haloalkyl, haloalkoxy, cyano, five or six membered heterocyclyl, or five or six membered heteroaryl ring.

10. The compound of claim 1 wherein the compound is:
2-(4-(diphenylamino)-2-methylpiperidin-1-yl)acetic acid;
2-(2-methyl-4-(phenyl(4-(trifluoro-methyl)phenyl)amino)piperidin-1-yl)acetic acid;
2-(2-methyl-4-(phenyl(3-(trifluoro-methyl)phenyl)amino)piperidin-1-yl)acetic acid;
or a pharmaceutically acceptable salt thereof.

11. A pharmaceutical composition comprising a compound of claim 1 or a pharmaceutically acceptable salt thereof, and a pharmaceutically acceptable excipient.

* * * * *